United States Patent
Mace et al.

(10) Patent No.: US 12,372,523 B2
(45) Date of Patent: Jul. 29, 2025

(54) PATTERNED DRIED BLOOD SPOT CARDS AND RELATED ARTICLES AND METHODS

(71) Applicant: Trustees of Tufts College, Medford, MA (US)

(72) Inventors: Charles R. Mace, Winchester, MA (US); Jessica E. Schilling, Bloomington, MN (US); Syrena C. Fernandes, Somerville, MA (US); Keith Baillargeon, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 1162 days.

(21) Appl. No.: 17/252,511

(22) PCT Filed: Jun. 19, 2019

(86) PCT No.: PCT/US2019/037913
§ 371 (c)(1),
(2) Date: Dec. 15, 2020

(87) PCT Pub. No.: WO2019/246207
PCT Pub. Date: Dec. 26, 2019

(65) Prior Publication Data
US 2021/0263027 A1    Aug. 26, 2021

Related U.S. Application Data

(60) Provisional application No. 62/688,707, filed on Jun. 22, 2018.

(51) Int. Cl.
*G01N 33/72* (2006.01)
*G01N 33/543* (2006.01)
*G01N 33/80* (2006.01)

(52) U.S. Cl.
CPC ....... *G01N 33/54386* (2013.01); *G01N 33/72* (2013.01); *G01N 33/80* (2013.01)

(58) Field of Classification Search
CPC .. G01N 33/54386; G01N 33/72; G01N 33/80; B01L 2300/0864; B01L 2300/0874; B01L 2300/0887
See application file for complete search history.

(56) References Cited

U.S. PATENT DOCUMENTS 5,262,067 A * 11/1993 Wilk ................ G01N 33/54386
                                                              210/732
5,846,438 A    12/1998 Pall et al.
(Continued)

FOREIGN PATENT DOCUMENTS

WO    WO 2017/123668 A1    7/2017
WO    WO 2018/099922 A1    6/2018

OTHER PUBLICATIONS

U.S. Appl. No. 17/252,503, filed Dec. 15, 2020, Wilson et al.
(Continued)

*Primary Examiner* — Jill A Warden
*Assistant Examiner* — John McGuirk
(74) *Attorney, Agent, or Firm* — Wolf, Greenfield & Sacks, P.C.

(57) ABSTRACT

Articles and methods involving fluidic devices are generally provided. In some embodiments, a fluidic device comprises a first layer comprising a central region in fluidic communication with an environment external to the fluidic device. The first layer may also comprise a first channel and a second channel in fluidic communication with the central region and extending radially outwards therefrom. The first and second channels may comprises first and second sample regions from which first and second samples can be removed from the fluidic device. In some embodiments, a fluidic device comprises a first layer and a second, filtration layer
(Continued)

configured to separate blood cells from plasma positioned between the environment external to the fluidic device and the first layer. In some embodiments, a fluidic device comprises a layer configured to distribute fluid from the region in fluidic communication with the environment external to the fluidic device laterally across the layer positioned between two porous, absorbent layers.

20 Claims, 26 Drawing Sheets

(56) References Cited

U.S. PATENT DOCUMENTS

| | | | |
|---|---|---|---|
| 6,036,659 | A | 3/2000 | Ray et al. |
| 6,274,041 | B1 | 8/2001 | Williamson et al. |
| 6,494,230 | B2 | 12/2002 | Chow |
| 6,623,860 | B2 | 9/2003 | Hu et al. |
| 6,739,576 | B2 | 5/2004 | O'Connor et al. |
| 7,318,912 | B2 | 1/2008 | Pezzuto et al. |
| 2002/0187072 | A1 | 12/2002 | Karp |
| 2002/0187560 | A1 | 12/2002 | Pezzuto et al. |
| 2006/0280029 | A1 | 12/2006 | Garstecki et al. |
| 2007/0092975 | A1* | 4/2007 | Potyrailo .............. G01N 21/78 436/169 |
| 2008/0241962 | A1 | 10/2008 | Wang |
| 2011/0123398 | A1 | 5/2011 | Carrilho et al. |
| 2012/0009662 | A1 | 1/2012 | Shen et al. |
| 2012/0322086 | A1 | 12/2012 | Garnier et al. |
| 2013/0130226 | A1 | 5/2013 | Lim et al. |
| 2014/0295472 | A1 | 10/2014 | Shevkoplyas et al. |
| 2015/0087079 | A1* | 3/2015 | Coffey ............ G01N 33/54306 436/501 |
| 2016/0038939 | A1 | 2/2016 | Min et al. |
| 2016/0090588 | A1 | 3/2016 | Lofquist et al. |
| 2018/0200677 | A1* | 7/2018 | Lee .................. B01L 3/502753 |
| 2019/0391130 | A1* | 12/2019 | Murray ............... B01D 63/088 |
| 2021/0268500 | A1 | 9/2021 | Wilson et al. |

OTHER PUBLICATIONS

PCT/US2019/037913, Sep. 5, 2019, International Search Report and Written Opinion.
International Search Report and Written Opinion for PCT/US2019/037913 mailed Sep. 5, 2019.
[No Author Listed], Simple spot check. GE Healthcare Life Sciecnes. Mar. 2010:2 pages [last accessed Apr. 25, 2017].
[No Author Listed], Vivid™ Plasma Separation Membrane. Pall Corporation. https://shop.pall.com/us/en/medical/advanced-materials/diagnostics/vivid-plasma-separation-membrane-zidgri7811s [last accessed Mar. 4, 2021].
Berry et al., Measurement of the hematocrit using paper-based microfluidic devices. Lab Chip. Oct. 7, 2016;16(19):3689-94. doi: 10.1039/c6lc00895j. Epub Sep. 7, 2016.
Carrilho et al., Understanding wax printing: a simple micropatterning process for paper-based microfluidics. Anal Chem. Aug. 15, 2009;81(16):7091-5. doi: 10.1021/ac901071p.
Cheng et al., Paper-based ELISA. Angew Chem Int Ed Engl. Jun. 28, 2010;49(28):4771-4. doi: 10.1002/anie.201001005.
Dechiara et al., An Open Software Platform for the Automated Design of Paper-Based Microfluidic Devices. Sci Rep. Nov. 24, 2017;7(1):16224. doi: 10.1038/s41598-017-16542-8.
Deraney et al., Multiplexed, Patterned-Paper Immunoassay for Detection of Malaria and Dengue Fever. Anal Chem. Jun. 21, 2016;88(12):6161-5. doi: 10.1021/acs.analchem.6b00854. Epub Jun. 1, 2016.
Fernandes et al., Beyond Wicking: Expanding the Role of Patterned Paper as the Foundation for an Analytical Platform. Anal Chem. Jun. 6, 2017;89(11):5654-5664. doi: 10.1021/acs.analchem.6b03860. Epub Apr. 26, 2017.
Fernandes et al., Comparison of three indirect immunoassay formats on a common paper-based microfluidic device architecture. Anal Methods. Jun. 2016;8:5204-11.
Fernandes et al., Fabrication of Three-dimensional Paper-based Microfluidic Devices for Immunoassays. J Vis Exp. Mar. 9, 2017;(121):55287. doi: 10.3791/55287.
Gao et al., Ultrasensitive paper based nucleic acid detection realized by three-dimensional DNA-AuNPs network amplification. Biosens Bioelectron. Jun. 15, 2017;92:529-535. doi: 10.1016/j.bios.2016.10.068. Epub Oct. 27, 2016.
Kim et al., Simple, miniaturized blood plasma extraction method. Anal Chem. Dec. 3, 2013;85(23):11501-8. doi: 10.1021/ac402735y. Epub Nov. 7, 2013.
Leuthold et al., New microfluidic-based sampling procedure for overcoming the hematocrit problem associated with dried blood spot analysis. Anal Chem. Feb. 17, 2015;87(4):2068-71. doi: 10.1021/ac503931g. Epub Jan. 30, 2015.
Li et al., A perspective on paper-based microfluidics: Current status and future trends. Biomicrofluidics. Mar. 2012;6(1):11301-1130113. doi: 10.1063/1.3687398. Epub Mar. 2, 2012.
Luckham et al., Bioactive paper dipstick sensors for acetylcholinesterase inhibitors based on sol-gel/enzyme/gold nanoparticle composites. Analyst. Aug. 2010;135(8):2028-35. doi: 10.1039/c0an00283f. Epub Jun. 30, 2010.
Mace et al., Manufacturing prototypes for paper-based diagnostic devices. Microfluid Nanofluid. 2014;16:801-9. doi: 10.1007/s10404-013-1314-6.
Martinez et al., Programmable diagnostic devices made from paper and tape. Lab Chip. Oct. 7, 2010;10(19):2499-504. doi: 10.1039/c0lc00021c. Epub Jul. 30, 2010.
Pollock et al., A paper-based multiplexed transaminase test for low-cost, point-of-care liver function testing. Sci Transl Med. Sep. 19, 2012;4(152):152ra129. doi: 10.1126/scitranslmed.3003981.
Riccardi et al., Covalent interlocking of glucose oxidase and peroxidase in the voids of paper: enzyme-polymer "spider webs". Chem Commun (Camb). Feb. 11, 2016;52(12):2593-6. doi: 10.1039/c6cc00037a. Epub Jan. 11, 2016.
Rosypal et al., Evaluation of a novel dried blood spot collection device (HemaSpot™) to test blood samples collected from dogs for antibodies to Leishmania infantum. Vet Parasitol. Sep. 15, 2014;205(1-2):338-42. doi: 10.1016/j.vetpar.2014.07.031. Epub Aug. 12, 2014.
Schneider et al., NIH Image to ImageJ: 25 years of image analysis. Nat Methods. Jul. 2012;9(7):671-5. doi: 10.1038/nmeth.2089.
Schonhorn et al., A device architecture for three-dimensional, patterned paper immunoassays. Lab Chip. Dec. 21, 2014;14(24):4653-8. doi: 10.1039/c4lc00876f. Epub Oct. 10, 2014.
Wilson et al., Reconfigurable Pipet for Customized, Cost-Effective Liquid Handling. Anal Chem. Sep. 5, 2017;89(17):8656-8661. doi: 10.1021/acs.analchem.7b02556. Epub Aug. 11, 2017.
Zhang et al., A dye-assisted paper-based point-of-care assay for fast and reliable blood grouping. Sci Transl Med. Mar. 15, 2017;9(381):eaaf9209. doi: 10.1126/scitranslmed.aaf9209. Epub Mar. 15, 2017.
[No Author Listed], Processing of Dried Blood Spots Standard Operating Procedure. ACTG/IMPAACT Lab Tech Committee. Mar. 19, 2012: 20 pages.
[No Author Listed], Who Manual for HIV Drug Resistance Testing Using Dried Blood Spot Specimens. World Health Organization. Jul. 2012: 26 pages.
Baillargeon et al., Patterned Dried Blood Spot Cards for the Improved Sampling of Whole Blood. ACS Meas Sci Au. Feb. 16, 2022;2(1):31-38. doi: 10.1021/acsmeasuresciau.1c00031. Epub Sep. 17, 2021.
Rottinghaus et al., Comparison of Ahlstrom grade 226, Munktell TFN, and Whatman 903 filter papers for dried blood spot specimen collection and subsequent HIV-1 load and drug resistance genotyping analysis. J Clin Microbiol. Jan. 2013;51(1):55-60. doi: 10.1128/JCM.02002-12. Epub Oct. 17, 2012.
Ryona et al., A Book-Type Dried Plasma Spot Card for Automated Flow-Through Elution Coupled with Online SPE-LC-MS/MS

(56) References Cited

OTHER PUBLICATIONS

Bioanalysis of Opioids and Stimulants in blood. Anal Chem. Nov. 15, 2016;88(22):11229-11237. doi: 10.1021/acs.analchem. 6b03691. Epub Nov. 2016.

* cited by examiner

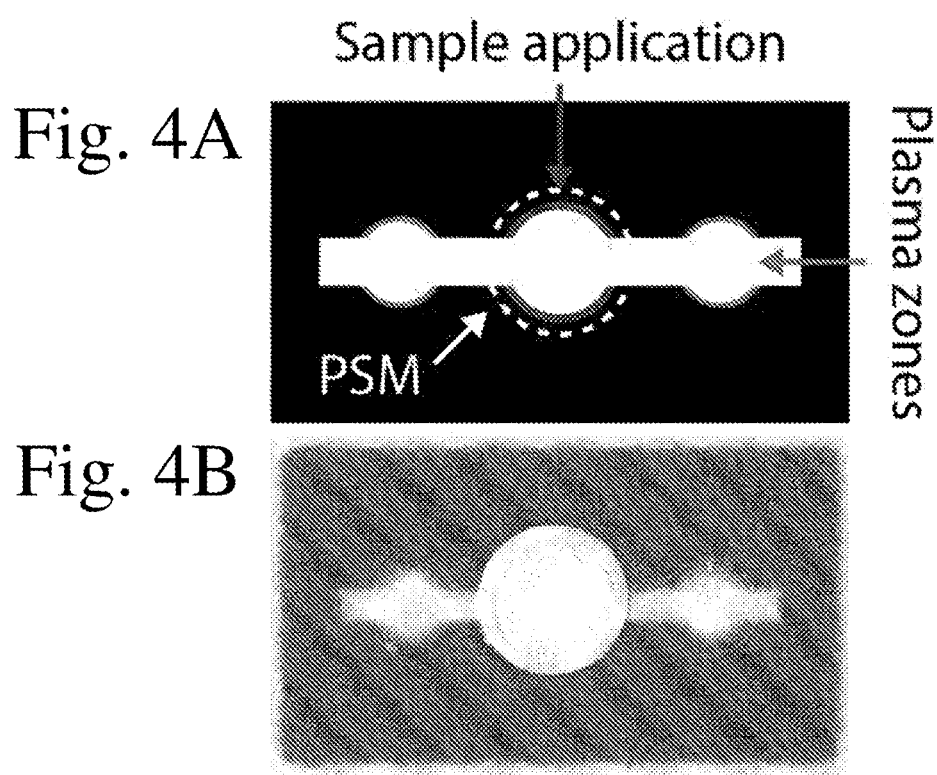

| Hct | [Hgb] (g/dL) | Extent of Lysis | SEM |
|---|---|---|---|
| 20% | 6.5 | 99% | 4% |
| 30% | 9.9 | 98% | 9% |
| 40% | 14.8 | 85% | 7% |
| 50% | 16.3 | 73% | 12% |

PATTERNED DRIED BLOOD SPOT CARDS AND RELATED ARTICLES AND METHODS

RELATED APPLICATIONS

This application is a national stage filing under 35 U.S.C. § 371 of international PCT application, PCT/US2019/037913, filed Jun. 19, 2019, and entitled "Patterned Dried Blood Spot Cards and Related Articles and Methods", which claims priority under 35 U.S.C. § 119(e) to U.S. Provisional Application No. 62/688,707, filed Jun. 22, 2018, and entitled "Patterned Dried Blood Spot Cards and Related Articles and Methods", which are incorporated herein by reference in their entirety for all purposes.

FIELD

Articles and methods involving fluidic devices are generally provided.

SUMMARY

Articles and methods involving fluidic devices are generally provided. The subject matter disclosed herein involves, in some cases, interrelated products, alternative solutions to a particular problem, and/or a plurality of different uses of one or more systems and/or articles.

Some aspects relate to fluidic devices. In some embodiments, a fluidic device comprises a layer comprising a porous, absorbent material. The layer comprises a central region in fluidic communication with an environment external to the fluidic device. The layer also comprises a first channel and a second channel in fluidic communication with the central region and extending radially outwards therefrom. The first channel comprises a first sample region from which a first sample can be removed from the fluidic device, and the second channel comprises a second sample region from which a second sample can be removed from the fluidic device.

In some embodiments, a fluidic device comprises a first layer comprising a porous, absorbent material and a second, filtration layer configured to separate blood cells from plasma. The first layer comprises a central region in fluidic communication with an environment external to the fluidic device and a channel in fluidic communication with the central region. The second layer comprises synthetic fibers and/or glass fibers and is positioned between the environment external to the fluidic device and the first layer.

In some embodiments, a fluidic device comprises a first layer, a second layer positioned beneath the first layer, and a third layer positioned beneath the second layer. The first layer comprises a porous, absorbent material and comprises a region in fluidic communication with an environment external to the fluidic device. The second layer is configured to distribute fluid from the region in fluidic communication with the environment external to the fluidic device laterally across the second layer. The third layer comprises a porous, absorbent material and comprises a channel.

Some aspects relate to methods. In some embodiments, a method comprises, in a layer comprising a porous, absorbent material, flowing a fluid sample from a central region through first and second channels extending radially outward from the central region to a first sample region and a second sample region equidistant from the central region.

In some embodiments, a method comprises passing a blood sample through a filtration layer configured to separate blood cells from plasma, retaining at least a portion of cells in the blood sample on a first side of the filtration layer, and transporting at least a portion of plasma in the blood sample away from the filtration layer through a channel in a first layer comprising a porous, absorbent material. The filtration layer comprises synthetic fibers and/or glass fibers.

In some embodiments, a method comprises flowing a sample vertically through a first layer comprising a porous, absorbent material into a second layer, flowing the sample laterally across the second layer, and flowing the sample through a channel in a third layer comprising a porous, absorbent material.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 4A shows a schematic depiction of a pDBS card, according to some embodiments;

FIG. 4B shows a photograph of a pDBS card, according to some embodiments;

DETAILED DESCRIPTION

Figure 1A:
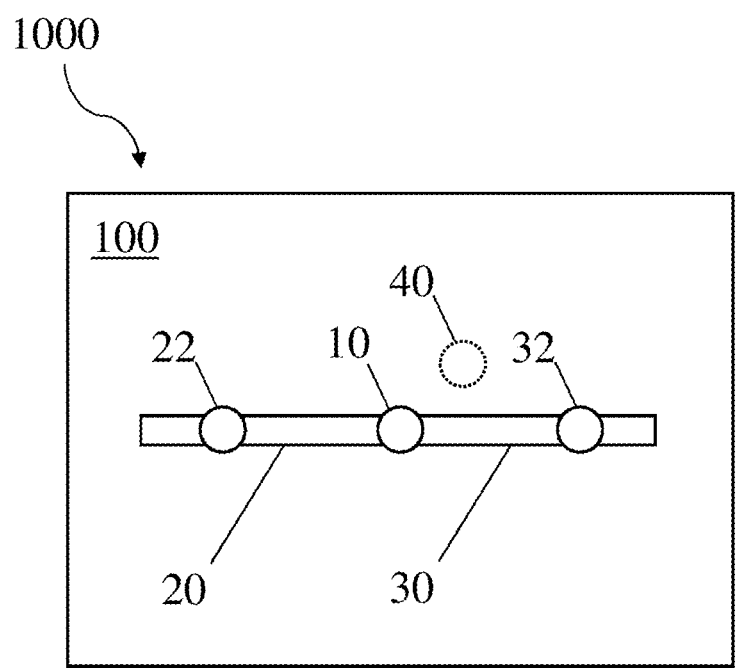
FIG. 1A shows a schematic depiction of a layer with an advantageous arrangement of channels and sample regions, according to some embodiments.

Articles and methods related to fluidic devices are generally provided. Some fluidic devices described herein may be configured to receive a fluid sample, and have a design that results in the preparation of high quality, reproducible samples from the fluid sample in one or more sample regions of the fluidic device. One or more of the sample regions may be configured to be removed from the fluidic device for later analysis of the sample therein, and/or one or more of the sample regions may be configured to perform one or more analyses of the sample(s) in the sample region(s). For example, in some embodiments, the fluidic device is a blood spot card with patterned channels, and a blood sample absorbed or adsorbed onto a surface of a channel is removed by a biopsy punch, e.g., punching a hole through the channel. In other embodiments, a sample is analyzed directly on the fluidic device and the sample is not removed from the device prior to analysis. These and other configurations are described in more detail below.

One example of a fluidic device design that may be advantageous for producing high quality, reproducible samples is an arrangement of sample regions at known positions with respect to the position of the fluidic device at which the fluid sample is initially received. For samples that include multiple components that flow to different extents and/or at different rates through the fluidic device, sample regions at the known positions may receive a fluid sample that has flowed a known distance from the region at which it was initially received. After flow of the fluid sample into and/or through the fluidic device, the characteristics of the sample retained in the sample regions may be predictable based on the positions and/or shapes of the sample regions. In some embodiments, a fluidic device comprises two or more sample regions. The two or more sample regions may be positioned equidistant from the position of the fluidic device at which the fluid sample is initially received, and so may retain samples that have substantially similar characteristics. In some examples, the two or more sample regions may extend radially outwards from a central region at which a fluid sample is initially received.

Another example of a fluidic device design that may be advantageous for producing high quality, reproducible samples is an arrangement of channels and sample regions such that the channels extend beyond the sample regions. When a fluid sample flows through a device, it may flow into a region, saturate the region, and then continue to flow through the saturated region into other regions. Regions that the fluid sample flows through (i.e., regions not positioned at the terminus of a flow path in the fluidic device) during filling of the fluidic device by the fluid sample may be saturated by the fluid sample once the fluidic device has been filled to capacity with the fluid sample. Regions that are saturated with the fluid sample may comprise a sample of the fluid sample with predictable characteristics, and so sample regions of the fluidic device configured to be saturated with fluid samples may retain samples of the fluid samples with predictable characteristics. A portion of a channel extending beyond a sample region that is filled during filling of the fluidic device may be filled by a fluid sample flowing through a saturated region. Filling these regions with a fluid sample flowing into a device may result in the formation of sample regions that are saturated with the fluid sample.

A third example of a fluidic device design that may be advantageous for producing high quality, reproducible samples is an arrangement of regions configured to have a fluid sample flow therethrough and regions configured not to have a fluid sample flow therethrough such that at least a portion of the regions configured not to have the fluid sample flow therethrough have a shape and/or size larger than that of a biopsy punch to be used with the fluidic device. For instance, at last a portion of the regions configured not to have the fluid sample flow therethrough may have a shape and size at least on the order of the shape and size of one or more sample regions present in the fluidic device. A technician retrieving samples from the fluidic device may use a biopsy punch to remove the sample regions from the device, and may clean the biopsy punch by punching through regions of the device into which the fluid sample has not flowed. Fluidic devices with this design may facilitate easy and rapid collection of uncontaminated samples therefrom.

A fourth example of a fluidic device design that may be advantageous for producing high quality, reproducible samples is the inclusion of a filtration layer. The filtration layer may be configured to separate components of the fluid sample from each other. Some of the components of the fluid sample may be retained by the filtration layer (e.g., on one side of the filtration layer) while other components pass through the filtration layer. For instance, a fluidic device may comprise a filtration layer configured to separate blood cells from plasma. Plasma in a blood sample may flow through the filtration layer (e.g., and into one or more channels of the fluidic device) while blood cells are retained by the filtration layer. The plasma passing through the filtration layer may flow to one or more sample regions, resulting in the formation of samples comprising plasma and either lacking blood cells or including a relatively small amount of blood cells at the sample regions. Samples rich in plasma and poor in blood cells (or lacking blood cells) may be advantageous for blood tests sensitive to plasma components. Formation of such samples in the fluidic device may allow tests sensitive to plasma components to be performed on the device (e.g., by reagents stored therein) without removal of the samples from the device or further processing.

A fifth example of a fluidic device design that may be advantageous for producing high quality, reproducible samples is the inclusion of a layer configured to distribute fluid laterally across the device. The layer configured to distribute fluid laterally across the device may be positioned between a layer at which the fluid sample is initially received and a layer comprising one or more sample regions. The layer configured to distribute fluid laterally across the device may distribute the fluid sample from the region of the first layer at which the fluid sample is initially received to the one or more sample regions and/or to one or more channels in fluidic communication with the one or more sample regions. The fluid sample may be distributed to the sample regions in a uniform manner; for instance, each sample region may receive portions of the fluid sample with substantially similar characteristics and/or may receive substantially similar amounts of the fluid sample.

FIG. 1A shows one non-limiting embodiment of a fluidic device comprising a layer with an advantageous arrangement of channels and sample regions. In FIG. 1A, a fluidic device 1000 comprises a layer 100. The layer 100 comprises a central region 10, a first channel 20 comprising a first sample region 22, and a second channel 30 comprising a second sample region 32. The central region may be in fluidic communication with an environment external to the fluidic device, e.g., the central region may be directly exposed to ambient air. Additionally or alternatively, the central region may be in fluidic communication with the first and/or second channels (and/or the first and/or second sample regions therein). In some embodiments, the fluidic device is designed such that the central region is configured to receive a sample (e.g., from the environment external to the fluidic device). The sample received by the central region may flow from the central region, through the first and second channels, and to the first and second sample regions. In some embodiments, and as shown illustratively in FIG. 1A, the first and second sample channels may extend radially outwards from the central region. As described above, this design may be advantageous for the formation of high quality, reproducible samples in the first and second sample regions.

In some embodiments, it may be possible to remove one or more samples from a fluidic device described herein. By way of example, with reference to FIG. 1A, in some embodiments a fluidic device comprises one or more sample regions (i.e., sample regions 22 and 32 in FIG. 1A) that facilitate removal of one or more samples from the fluidic device. The sample(s) and sample region(s) may be removed from the fluidic device together (e.g., by way of a biopsy punch, by way of peeling), or the sample(s) may be removed from the fluidic device without also removing the sample region(s). In some embodiments, a fluidic device comprises one or more regions other than a sample region that may be removed therefrom. For instance, a fluidic device may comprise a region that may be removed therefrom by a biopsy punch in a procedure by which the biopsy punch is cleaned. With reference to FIG. 1A, a layer 100 of a fluidic device 1000 may comprise a region 40 that may be removed by a biopsy punch. A technician retrieving samples from the sample regions 22 and 32 in FIG. 1A may punch one of the sample regions out of the device (e.g., a first sample region 22), punch the region 40 out of the device to clean the biopsy punch, and then punch the other sample region out of the device (e.g., second sample region 32). Punching portions of the device other than sample regions (e.g., regions of the device through which the fluid sample has not flowed) may reduce cross-contamination between samples punched from different sample regions.

It should be understood that the fluidic device shown in FIG. 1A is not limiting, and that modifications to the fluidic device shown in FIG. 1A are also possible. For example, a fluidic device may comprise more than two channels in fluidic communication with a central region. The fluidic device may comprise, for example, three, four, five, six, or more channels in fluidic communication with the central region (e.g., each extending radially from the external region).

Figure 1B:
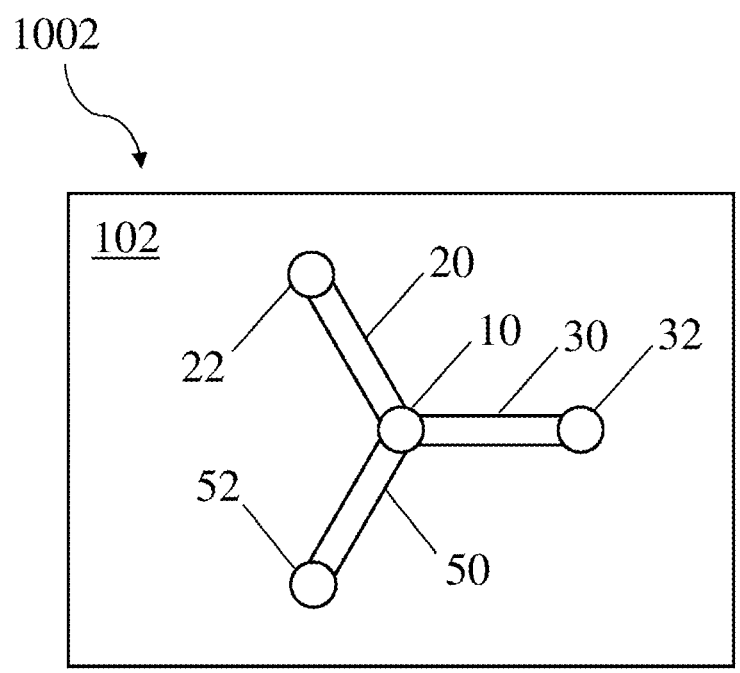
FIG. 1B shows a schematic depiction of a layer comprising three channels and three sample regions, according to some embodiments.

FIG. 1B shows one example of a fluidic device that differs from the fluidic device shown in FIG. 1A. In FIG. 1B, a fluidic device 1002 comprises a layer 102 comprising a first channel 20, a second channel 30, and a third channel 50. Each channel may have the same length (e.g., as is shown in FIGS. 1A and 1B), or two or more channels may have different lengths. The channels may extend radially from the central region such that they are positioned radially symmetrically around the central region (e.g., as shown in FIGS. 1A and 1B), may extend radially from the central region such that they are not positioned radially symmetrically around the central region (e.g., one pair of adjacent channels may intersect in the central region at an angle other than that of another pair of adjacent channels), and/or may extend from the central region in directions other than radial directions (e.g., two or more channels may comprise regions that are parallel to each other). Other arrangements of the channels are also possible.

As another example, the arrangement of the sample regions with respect to the channels may be other than that shown in FIG. 1A. While in some embodiments, like the embodiment shown in FIG. 1A, one or more channels comprising a sample region may extend beyond the sample regions therein, some channels may terminate in sample regions, like the embodiment shown in FIG. 1B. In FIG. 1B, the first channel 20 comprises a first sample region 22, the second channel 30 comprises a second sample region 32, and the third channel 50 comprises a third sample region 52.

As shown illustratively in both FIGS. 1A and 1B, the same regions are equidistant from the central region in some embodiments. In other embodiments, two sample regions may be positioned at different distances from the central region. In some embodiments, like the embodiments shown in FIGS. 1A and 1B, each channel comprising a sample region includes a single sample region. In other embodiments, a fluidic device may comprise one or more channels lacking a sample region and/or one or more channels comprising two or more sample regions (e.g., a channel may be configured such that a fluid sample flowing therethrough flows through a first sample region and then into a second sample region).

In some embodiments, like the embodiments shown illustratively in FIGS. 1A and 1B, a fluidic device comprises channels each including one sample region. However, a fluidic device may comprise one or more channels each comprising a number of sample regions other than one. For instance, some channels may comprise zero sample regions, two sample regions, three sample regions, or another number of sample regions. It should also be understood that a fluidic device may comprise sample regions having uniform shapes and volumes (e.g., as shown in FIGS. 1A and 1B), or that a fluidic device may comprise two sample regions that have differing shapes and/or volumes. The sample regions typically have volumes suitable for retaining an amount of a fluid sample advantageous for performing one or more measurements thereon and/or may have shapes suitable for removing from the fluidic device with biopsy punches. In some embodiments, one or more sample regions extend laterally outwards from the channels in which they are positioned. However, other sample region volumes and shapes are also possible.

FIGS. 1A and 1B show fluidic devices which comprise a single central region and channels extending therefrom. In such fluidic devices, a single fluid sample may be received by the device and flowed to one or more sample regions therein. Some fluidic devices may be configured to receive more than one fluid sample. These fluidic devices may comprise more than one central region, and in some embodiments, the multiple central regions are not in fluidic communication with each other through the fluidic device. Each of these fluidically disconnected sample regions may be in fluidic communication with one or more sample regions. The fluidic device may be configured such that each central region is configured to receive a different fluid sample and such that the fluid samples received by each central region flows to the sample region(s) with which they are in fluidic communication. These fluidic devices may be configured to receive multiple fluid samples (e.g., blood samples from different individuals, different blood samples from a single individual) and form multiple samples of each fluid sample received. Each sample formed may be high quality and/or reproducible.

Figure 1C:
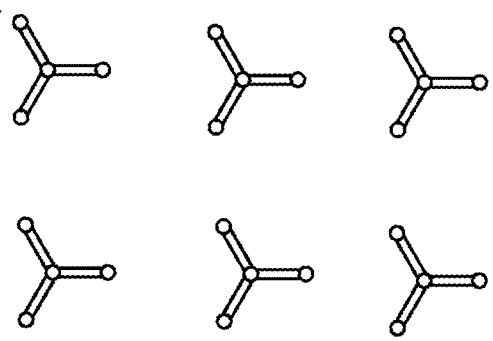
FIG. 1C shows one non-limiting embodiment of a fluidic device configured to receive multiple fluid samples, according to some embodiments.

FIG. 1C shows one non-limiting embodiment of a fluidic device configured to receive multiple fluid samples. In FIG. 1C, a fluidic device 1004 comprises a layer 104 comprising a plurality of channel configurations shown in FIG. 1B. The channel configurations include central regions not in fluidic communication with each other through the fluidic device, but each central region being in fluidic communication with multiple channels. Each channel with which a central region is in fluidic communication comprises a sample region.

In some embodiments, a layer shown in any one of FIGS. 1A-IC may be a layer of a fluidic device as described elsewhere herein (e.g., a layer of a fluidic device comprising a filtration layer and/or a layer of a fluidic device comprising a layer configured to distribute fluid within the fluidic device, both of which are described in further detail below). It should also be understood that the fluidic devices described herein may comprise more layers than shown herein (e.g., they may comprise one or more additional layers, such as those described elsewhere herein).

As described above, a fluidic device may comprise more than one layer. In some embodiments, a fluidic device comprises one or more layers comprising channels and/or sample regions (e.g., as described above with respect to FIGS. 1A-1C), e.g., first layer(s). The fluidic device further comprises one or more layers (e.g., second layer(s)) configured to provide the first layer(s) with a fluid sample. The second layer may have one or more advantageous properties, as described in more detail below. For example, a fluidic device may comprise a filtration layer (e.g., a second layer). The filtration layer may be configured to separate two or more components of a fluid sample from each other. The filtration layer may be configured to pass some portions of the fluid sample and retain other portions of the fluid sample. In the case of fluidic devices configured to form samples comprising blood, it may be desirable for the samples to be relatively rich in certain portions of blood and relatively poor in (or lacking entirely) others. For instance, it may be desirable for a filtration layer to be configured to separate blood cells from plasma. Some advantageous filtration layers may be configured to allow a relatively high proportion of the plasma in blood to pass therethrough and may also be configured to retain a relatively high proportion of the cells in blood. Other types of filtration layers (e.g., that filter blood in a different manner, that are configured to filter one or more components of another type of fluid sample) may also be employed.

In some embodiments, a fluidic device may comprise a filtration layer and may be configured to transport a fluid sample that has been filtered by the filtration layer away from the filtration layer. The fluid sample may be transported, for example, to a sample region. By way of example, a fluidic device may comprise a filtration layer configured to separate blood cells from plasma, and may be configured to transport plasma passed through the filtration layer away from the filtration layer. Some methods may comprise forming samples comprising plasma by passing a blood sample through a filtration layer configured to separate blood cells from plasma, retaining at least a portion of the cells on a first side of the filtration layer (e.g., a side of the filtration layer closer to an environment external to the fluidic device), and transporting at least a portion of the plasma away from the filtration layer. The plasma may be transported away from the filtration layer by a channel (e.g., in a first layer positioned beneath the filtration layer) and/or may be transported to one or more sample regions (e.g., in the first layer positioned beneath the filtration layer).

Figure 2A:
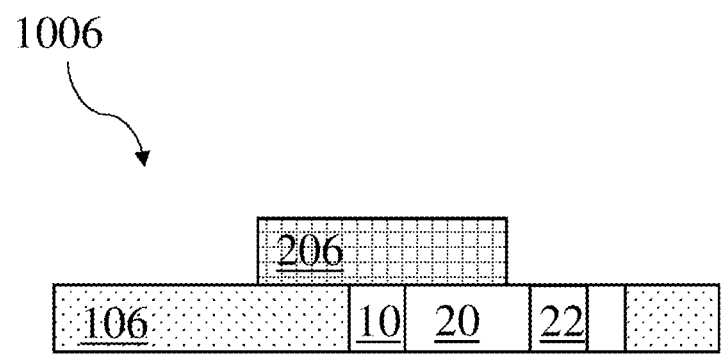
FIGS. 2A and 2B show two different views of one example of a fluidic device comprising a filtration layer and a layer comprising a channel and a sample region, according to some embodiments.
Figure 2B:
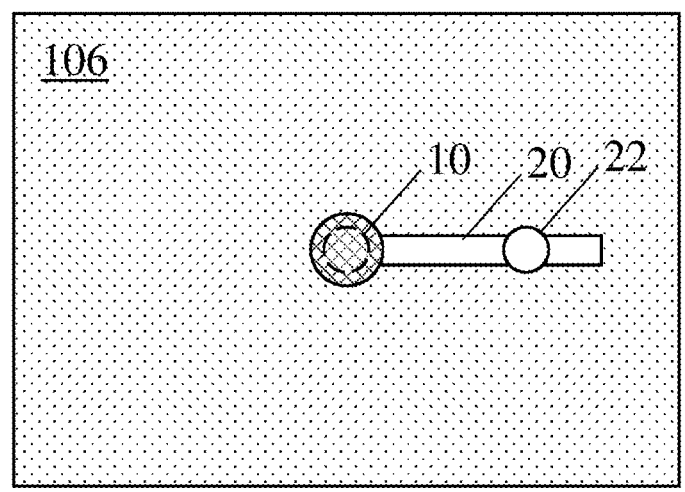

FIGS. 2A and 2B show two different views of one example of a fluidic device comprising a filtration layer and a layer comprising a channel and a sample region. In FIGS. 2A and 2B, fluidic device 1006 comprises a first layer 106 and a second layer 206. The first layer 106 comprises a central region 10 and a first channel 20. The first channel further comprises a sample region 22. The central region may be in fluidic communication with an environment external to the fluidic device and/or with the first channel. For example, the central region may be exposed to ambient air. The second layer 206 is a filtration layer. In some embodiments, as shown in FIGS. 2A and 2B, the filtration layer may be adjacent or directly adjacent the first layer. The filtration layer may be positioned between the environment external to the fluidic device and the first layer, and/or may be an external layer (e.g., the top-most or bottom-most layer of the fluidic device).

As used herein, when a layer is referred to as being "adjacent" another layer, it can be directly adjacent the layer, or an intervening layer also may be present. A layer that is "directly adjacent" another layer is positioned with respect to the layer such that no intervening layer is present.

In some embodiments, like that shown illustratively in FIGS. 2A and 2B, a fluidic device comprises a filtration layer that extends across a portion, but not all, of a layer comprising a channel and/or a sample region. The filtration layer may extend across a portion of the fluidic device configured to receive a fluid sample from an environment external to the fluidic device, such as a central region, but not over portions of the fluidic device not configured to receive a fluid sample from an environment external to the fluidic device (e.g., portions of the fluidic device configured to receive a fluid sample from the central region). Filtration layers may be relatively expensive and/or may be commercially available in standard sizes. Accordingly, it may be beneficial to position the filtration layers where beneficial, such as in regions where they may filter a fluid sample entering the fluidic device, while not having them extend over regions in which they would not enhance the performance of the fluidic device, such as regions that they would merely cover without providing any other benefits. In some embodiments, however, a filtration layer may extend over the entirety of a layer to which it is adjacent, such as a layer comprising a channel and/or a sample region.

In some embodiments, a fluidic device comprises a filtration layer that is reversibly attached to another layer of the device. The filtration layer may be positioned on a first layer, and may be capable of being removed from the first layer by hand (e.g., by peeling), without the use of specialized tools, and/or without destroying the first layer. For instance, the filtration layer may be reversibly attached to the fluidic device by way of an adhesive that allows delamination of the filtration layer from the fluidic device. Non-limiting examples of suitable adhesives include tapes, spray-on adhesives, double-sided films, screen-printed glues, and polymeric adhesives. The adhesive may take the form of a layer and/or film (e.g., a continuous layer, a discontinuous layer), or may be present in a non-layer and/or non-film form. In some embodiments, the filtration layer may be permanently attached to the fluidic device (e.g., attached in a manner other than reversibly, such as integrally attached to the device). Permanent or integral attachment may be facilitated by the use of permanent adhesives.

In some embodiments, a fluidic device comprises a filtration layer and further comprises a layer disposed on the filtration layer. The layer disposed on the filtration layer may prepare a fluid sample for filtration (e.g., a sample preparation layer). For example, the layer disposed on the filtration layer may be configured to lyse blood, and the filtration layer may be configured to pass the lysate and retain unlysed cells and/or lysed cell fragments.

Figure 3A:
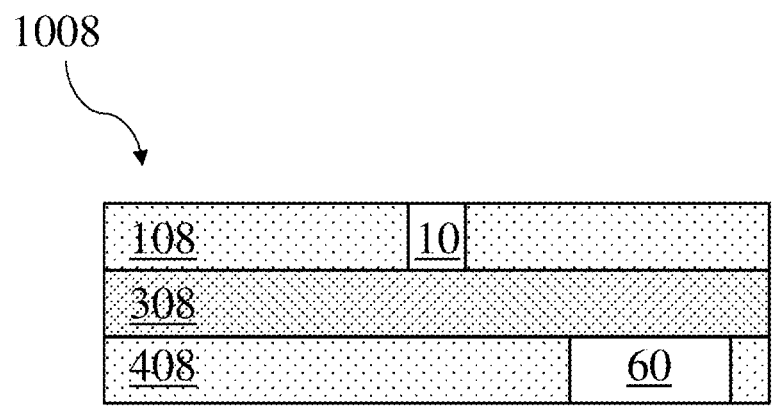
FIGS. 3A-3B show two views of one non-limiting example of a fluidic device comprising a layer configured to distribute fluid within the fluidic device, according to some embodiments.
Figure 3B:
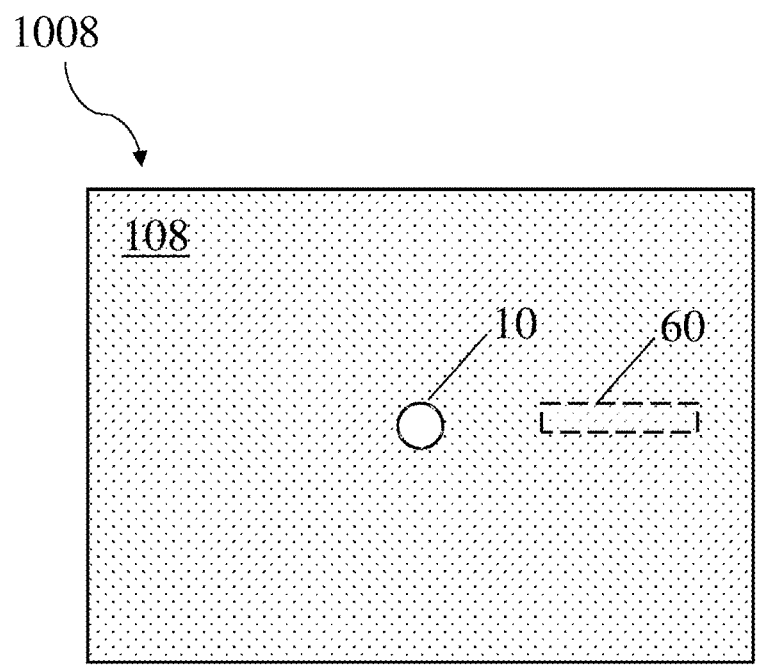

As also described above, a fluidic device may comprise a layer configured to distribute fluid within the fluidic device. FIGS. 3A-3B show two views of one non-limiting example of a fluidic device comprising a layer with this property. In FIGS. 3A-3B, fluidic device 1008 comprises a first layer 108 comprising a central region 10, a second layer 308 configured to distribute fluid (e.g., a fluid distribution layer) within the fluidic device, and a third layer 408 comprising a channel 60. In some embodiments, the fluid distribution layer does not include a channel. The central region may be in fluidic communication with an environment external to the fluidic device. In FIGS. 3A-3B, the second layer 308 is positioned beneath (e.g., directly adjacent) the first layer, and the third layer 408 is positioned beneath (e.g., directly adjacent) the second layer 308. A fluid sample flowing through the fluidic device shown in FIGS. 3A-3B may be received by the fluidic device at the central region 10, flow into the second layer 308 (e.g., by flowing vertically through the first layer 108), flow laterally across the second layer 308, and then flow into the third layer 408. After flowing into the third layer 408, the fluid sample may flow through one or more channels therein (e.g., channel 60).

In some embodiments, a layer used to distribute a fluid to another region of the device, such a fluid distribution layer (e.g., the second layer in FIGS. 3A-3B) is not patterned with one or more channels (e.g., the layer may be a homogenous layer with no channels). Advantageously, such a layer may be relatively less expensive to fabricate and/or may be formed of one or more materials that quickly distributes or spreads a fluid to a desired location (or across the entire layer). In other embodiments, however, the second layer may include patterned channels to localize a fluid within the layer.

In some embodiments, a fluid sample may flow into a fluidic device and across a region that extends for a relatively small distance laterally across the fluidic device (e.g., the central region may occupy a relatively small portion of the total area of the first layer), but the fluid sample may flow into a relatively large portion of the third layer of the fluidic device (e.g., it may flow into a relatively large portion of the total area of the third layer). Additionally or alternatively, the fluid sample may flow into regions of the third layer distributed across relatively large portions of the third layer (e.g., it may flow into one or more regions of the third layer, optionally not in fluidic communication with each other, that together span relatively large portions of the third layer and/or are separated from each other by relatively large portions of the third layer). The third layer may comprise one or more sample regions (e.g., as regions within one or more channels). The sample regions may be spatially separated from each other, and the second layer may distribute the fluid sample to the sample region(s) and/or to one or more channels in fluidic communication with the sample region(s). The fluid sample retained in the sample regions may form samples that are reproducible and/or of high quality.

Figure 3C:
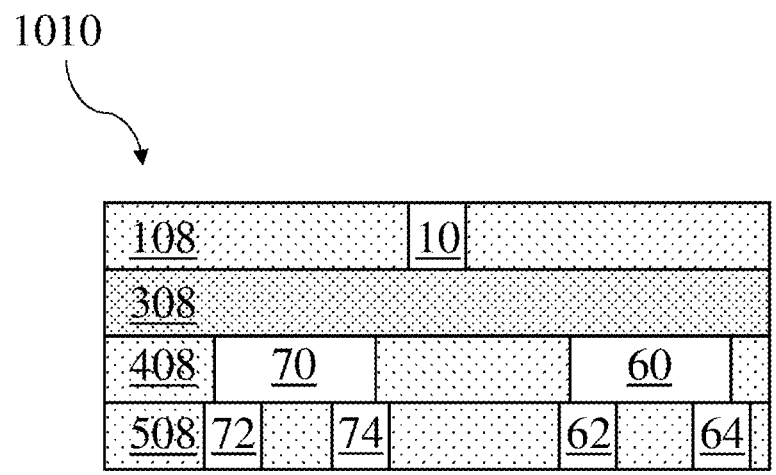
FIGS. 3C-3D show two views of one non-limiting embodiment of a fluidic device comprising four layers, according to some embodiments.
Figure 3D:
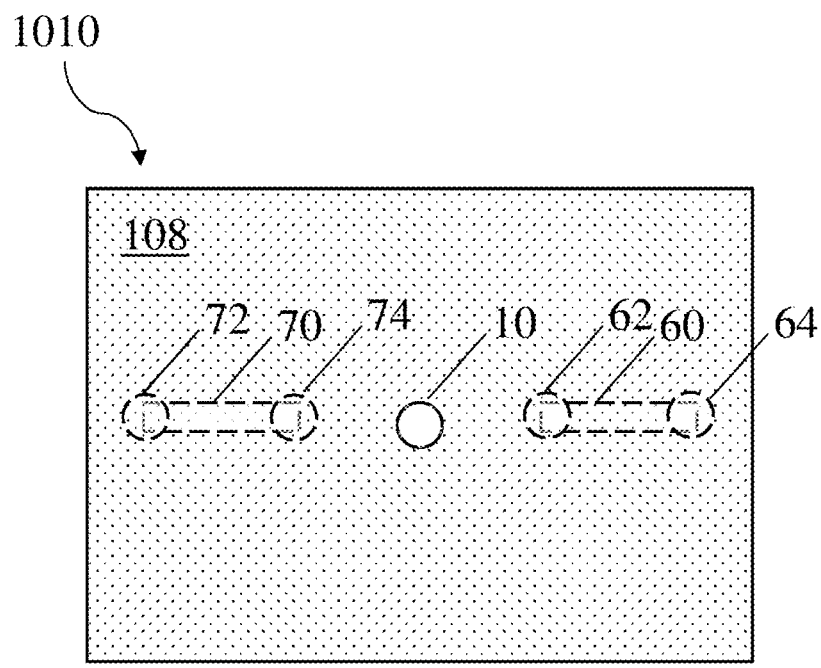

In some embodiments, a fluidic device comprises a layer configured to distribute fluid within the fluidic device (e.g., a fluid distribution layer) and further comprises three or more additional layers. For instance, as described above with reference to FIG. 3A, a fluidic device may comprise a layer configured to distribute fluid within the fluidic device positioned between two other layers, and may further comprise one or more additional layers. FIGS. 3C-3D show two views of one non-limiting embodiment of a fluidic device comprising four layers. In FIGS. 3C-3D, a fluidic device 1010 comprises a first layer 108 comprising a central region 10, a second layer 308 configured to distribute fluid within the fluidic device (e.g., a fluid distribution layer), a third layer 408 comprising a first channel 60 and a second channel 70, and a fourth layer 508 comprising a first sample region 62, a second sample region 64, a third sample region 72, and a fourth sample region 74. A fluid sample flowing through the fluidic device shown in FIGS. 3C-3D may be received by the fluidic device at the central region 10, flow into the second layer 308, flow laterally across the second layer 308, and then flow into the third layer 408. After flowing into the third layer 408, the fluid sample may flow through the channels 60 and 70 therein and then into the sample regions 62, 64, 72, and 74 in the fourth layer 508.

In some embodiments, a fluidic device comprises a cover layer. Advantageously, the cover layer may enclose and/or protect the fluidic device in which it is positioned. It may be impermeable to one or more fluids to be introduced into the fluidic device, may be impermeable to one or more components of an environment external to the fluidic device, may strengthen the fluidic device, and/or may decrease the tendency of the fluidic device to be damaged during handling.

A fluidic device may comprise a cover layer that is the uppermost layer and/or a cover layer that is the lowermost layer. The cover layer may further comprise one or more openings, which may be in fluidic communication with one or more features of a layer to which it is adjacent. For instance, an uppermost cover layer may comprise one or more openings in fluidic communication with a central region and/or a channel of a layer therebeneath. In some embodiments, a cover layer lacks openings and prevents fluidic communication between a layer to which it is adjacent an environment external to the fluidic device through the cover layer. For instance, a lowermost cover layer may seal the bottom of the fluidic device from direct fluidic communication with an environment beneath the fluidic device.

In some embodiments, a fluidic device comprises a wick pad. The wick pad may be a relatively thick, absorbent layer configured to wick and absorb any excess fluid from a layer to which it is adjacent. For instance, in some embodiments, a wick pad may be positioned as the lowermost layer (or the lowermost layer other than the cover layer) and may be configured to wick excess fluid from the layer beneath which it is positioned. This may be beneficial, for instance, in the case where a large amount of fluid is applied to the fluidic device. This large amount of fluid may cause an amount of fluid to flow to the sample regions that is larger than the amount desired for later analysis thereof. A wick pad in fluidic communication with such sample regions (e.g., positioned directly therebeneath) may wick fluid from these sample regions to an extent such that the desired amount of fluid is retained therein.

As described above, fluidic devices described herein may comprise one or more channels. The channels may be open channels (e.g., the channels may be open along two sides, or open along one side), or the channels may be enclosed. The channels may have a variety of suitable dimensions. In some embodiments, one or more channels are present in a layer, and the channel extends through the thickness of the layer. In other words, some channels may have the same thickness as the layers in which they are positioned. In some embodiments, one or more channels may have dimensions that aid in metering of a fluid sample. The channel(s) may have a volume, dimension, and/or shape that promotes flow of a desired volume of the fluid sample therein and/or therethrough.

A fluidic device may comprise a channel with a thickness or height of greater than or equal to 50 microns, greater than or equal to 75 microns, greater than or equal to 100 microns, greater than or equal to 125 microns, greater than or equal to 150 microns, greater than or equal to 200 microns, greater than or equal to 250 microns, greater than or equal to 300 microns, greater than or equal to 400 microns, greater than or equal to 500 microns, greater than or equal to 750 microns, or greater than or equal to 1 mm. The fluidic device may comprise a channel with a thickness or height of less than or equal to 2 mm, less than or equal to 1 mm, less than or equal to 750 microns, less than or equal to 500 microns, less than or equal to 400 microns, less than or equal to 300 microns, less than or equal to 250 microns, less than or equal to 200 microns, less than or equal to 150 microns, less than or equal to 125 microns, less than or equal to 100 microns, or less than or equal to 75 microns. Combinations of the above-referenced ranges are also possible (e.g., greater than or equal to 50 microns and less than or equal to 2 mm, greater than or equal to 50 microns and less than or equal to 500 microns, or greater than or equal to 50 microns and less than or equal to 100 microns). Other ranges are also possible.

Channels in fluidic devices may have a variety of suitable widths. In some embodiments, a fluidic device comprises a channel with a width of greater than or equal to 500 microns, greater than or equal to 750 microns, greater than or equal to 1 mm, greater than or equal to 1.5 mm, greater than or equal to 2 mm, greater than or equal to 2.5 mm, greater than or equal to 3 mm, greater than or equal to 3.5 mm, greater than or equal to 4 mm, or greater than or equal to 4.5 mm. The fluidic device may comprise a channel with a width of less than or equal to 5 mm, less than or equal to 4.5 mm, less than or equal to 4 mm, less than or equal to 3.5 mm, less than or equal to 3 mm, less than or equal to 2.5 mm, less than or equal to 2 mm, less than or equal to 1.5 mm, less than or equal to 1 mm, or less than or equal to 750 microns. Combinations of the above-referenced ranges are also possible (e.g., greater than or equal to 500 microns and less than or equal to 5 mm, or greater than or equal to 2 mm and less than or equal to 5 mm). Other ranges are also possible.

Channels in fluidic devices may have a variety of suitable aspect ratios (i.e., ratios of the channel length to the channel width). In some embodiments, a fluidic device comprises a channel with an aspect ratio of greater than or equal to 3:1, greater than or equal to 5:1, greater than or equal to 7:1, greater than or equal to 10:1, greater than or equal to 20:1, greater than or equal to 50:1, or greater than or equal to 70:1. The fluidic device may comprise a channel with an aspect ratio of less than or equal to 100:1, less than or equal to 70:1, less than or equal to 50:1, less than or equal to 20:1, less than or equal to 10:1, less than or equal to 7:1, or less than or equal to 5:1. Combinations of the above-referenced ranges are also possible (e.g., greater than or equal to 3:1 and less than or equal to 100:1). Other ranges are also possible.

Channels in fluidic devices described herein may have a variety of suitable volumes. In some embodiments, it may be desirable for a channel to have a volume such that it is configured to receive a desirable amount of a fluid sample. For instance, a channel may have a volume such that a sample region therein becomes saturated with an appropriate amount of a fluidic sample for one or more analyses after exposure to the fluid sample. In some embodiments, a channel may have a relatively low volume, so that the channel and/or one or more sample regions therein may be saturated after the channel has received a relatively low volume of the fluidic sample. This may be desirable for fluid samples that are expensive and/or difficult to procure large amounts of.

In some embodiments, a fluidic device comprises a channel with a volume of greater than or equal to 1 μL, greater than or equal to 2 μL, greater than or equal to 5 μL, greater than or equal to 10 μL, greater than or equal to 15 μL, greater than or equal to 20 μL, greater than or equal to 30 μL, greater than or equal to 40 μL, greater than or equal to 50 μL, greater than or equal to 75 μL, greater than or equal to 100 μL, greater than or equal to 150 μL, greater than or equal to 200 μL, greater than or equal to 300 μL, greater than or equal to 400 µL, greater than or equal to 500 µL, or greater than or equal to 750 µL. The fluidic device may comprise a channel with a volume of less than or equal to 1 mL, less than or equal to 750 µL, less than or equal to 500 µL, less than or equal to 400 µL, less than or equal to 300 µL, less than or equal to 200 µL, less than or equal to 150 µL, less than or equal to 100 µL, less than or equal to 75 µL, less than or equal to 50 µL, less than or equal to 40 µL, less than or equal to 30 µL, less than or equal to 20 µL, less than or equal to 15 µL, less than or equal to 10 µL, less than or equal to 5 µL, or less than or equal to 2 µL. Combinations of the above-referenced ranges are also possible (e.g., greater than or equal to 1 µL and less than or equal to 50 µL). Other ranges are also possible. In some embodiments, a channel comprises a sample region with a volume in one or more of the ranges described above (e.g., a channel may comprise a sample region with a volume of greater than or equal to 1 µL and less than or equal to 1 mL, greater than or equal to 1 µL and less than or equal to 50 µL, or greater than or equal to 100 µL and less than or equal to 300 µL).

In some embodiments, a fluidic device comprises two or more channels that have relatively similar volumes. The channels with the relatively similar volumes may be in the same layer (e.g., two or more channels that extend radially from a central region may have relatively similar volumes). Relatively similar volumes of a fluidic sample may flow into and/or through channels with relatively similar volumes, resulting in the retention of relatively similar samples in the channels. In some embodiments, two channels (e.g., two channels positioned in the same layer, two channels extending radially from a central region) may have volumes that differ by no more than 500%, no more than 400%, no more than 300%, no more than 200%, no more than 100%, no more than 50%, no more than 25%, no more than 10%, no more than 5%, no more than 2%, or no more than 1%.

In some embodiments, a fluidic device may comprise two or more channels that have volumes differing outside of the ranges described above (e.g., channels in different layers of the fluidic device). It should be understood that a fluidic device may comprise two or more channels that have relatively similar volumes (e.g., volumes that differ by an amount in one or more of the ranges described above) and may comprise two or more channels that have relatively different volumes (e.g., volumes that differ by an amount outside of one or more of the ranges described above.

As described above, channels described herein may comprise one or more sample regions. The sample regions may be regions configured to collect a fluidic sample in an appropriate amount and at an appropriate quality such that the region can be removed for later analysis, and/or may be configured to perform one or more analyses on a fluid sample in situ. The analyses performed in situ may produce signals that can easily be detected in situ, such as by eye or by a detector (e.g., colorimetric signals). In some embodiments, a single fluidic device may comprise two or more sample regions configured to perform different types of analyses. For instance, a single fluidic device may comprise a first sample region configured to perform a first type of analysis (e.g., a measurement of a level of hematocrit) and a second sample region configured to perform a second type of analysis (e.g., a measurement of a level of hemoglobin). The sample regions configured to perform the differing types of analysis may be in fluidic communication (e.g., they may both be configured to receive a fluidic sample from a single central region), or they may not be in fluidic communication (e.g., they may be configured to receive a fluidic sample from different central regions).

A fluidic device may comprise sample regions that are positioned in a single layer (e.g., a layer comprising two or more sample regions), and/or that are positioned in two or more layers (e.g., a fluidic device may comprise two or more layers comprising sample regions). When a fluidic device comprises two or more layers comprising sample regions, the layers comprising the sample regions may be directly adjacent to one another, or one or more intervening layers may be positioned between the layers comprising the sample regions (e.g., other layer(s) also comprising sample regions, layer(s) lacking sample regions, layers configured to distribute fluid within the fluidic device). Some embodiments may involve flowing a fluid sample through a fluidic device comprising multiple layers comprising sample regions such that the fluid sample is split into portions and such that each portion flows into a different sample region. In some embodiments, prior to flowing into a sample region, a portion of the fluid sample may flow through a layer comprising sample regions (e.g., through its thickness), but does not flow into the sample regions in that layer. Other portions of the fluid sample may flow into a sample region in that layer, but then do not flow into layers positioned beneath that layer. Fluidic devices configured for fluid flow of this type are also contemplated.

Several types of analyses and appropriate reagents for performing these analyses are described below. It should be understood that these analyses and reagent combinations are not limiting, and that some sample regions may comprise reagents configured to perform types of analyses not listed below (e.g., a measurement of folic acid, glucose-6-phosphate dehydrogenase) and some sample regions may be configured to perform a type of analysis listed below but may comprise a different set of reagents than those listed below. The analyses may be performed on blood that has been at least partially (e.g., entirely, or less than entirely) lysed, may be performed on blood that has not been lysed, and/or may be performed on fluid samples other than blood. The sample regions may be configured to lyse blood and/or to perform analyses on blood that has been lysed.

Reagents stored in a fluidic device (e.g., in a sample region) may be stored therein in a variety of ways. Non-limiting examples of ways that reagents may be stored in the fluidic device include being adsorbed onto a material present in the fluidic device (e.g., fibers in a fibrous sample region), absorbed into a material present in the fluidic device (e.g., fibers in a fibrous sample region), and/or in a gel present in the fluidic device (e.g., in a sample region). In some embodiments, the reagents may be deposited onto one or more fibers in the fluidic device (e.g., one or more fibers in a fibrous region or channel). The reagents may be stored in the fluidic device as solids. The solids may be present in a matrix, such as a matrix comprising a protein (e.g., bovine serum albumin) and/or a sugar (e.g., sucralose, trehalose). In some embodiments, one or more reagents stored in a fluidic device (e.g., as solids) may be reconstituted and/or dissolved in a fluid and/or a portion of a fluid sample flowing therethrough. For example, a fluid and/or a portion of a fluidic sample may flow through a disconnected region comprising one or more reagents, and at least a portion of the one or more reagents may dissolve in the fluid and/or the portion of the fluidic sample as it flows therethrough.

In some embodiments, a sample region may comprise one or more reagents suitable for performing a measurement of a level of hematocrit in blood and/or plasma. For example, the sample region may comprise: (1) an anticoagulant, such as ethylenediaminetetraacetic acid; and/or (2) sodium chloride.

In some embodiments, a sample region may comprise one or more reagents suitable for performing a measurement of a level of hemoglobin in blood and/or plasma. For example, the sample region may comprise: (1) an oxidizing agent, such as ammonium persulfate; (2) a buffer, such as acetate buffer; (3) a reducing agent, such as ascorbic acid; (4) a colorimetric indicator, such as bathophenanthroline, ferrozine, 1,10-phenanthroline, or Drabkin's reagent; (5) a surfactant, such as O,O'-Bis(2-aminopropyl) propylene glycol-block-polyethylene glycol-block-polypropylene glycol (e.g., Jeffamine), poly(diallyldimethylammonium chloride), or polyoxyethylene (23) lauryl ether (e.g., Brij23, Brij 35, C12E23); and/or (6) a cell lysis reagent, such as saponin. When Drabkin's reagent is employed as the colorimetric indicator, the presence of yellow or orange in the sample region may be indicative of high levels of hemoglobin and/or the presence of red in the sample region may be indicative of low levels of hemoglobin. The color of the sample region may be analyzed with a spectrophotometer.

In some embodiments, a sample region may comprise one or more reagents suitable for performing an immunoassay, such as an immunoassay for malaria, HIV, dengue, hCG (e.g., to determine pregnancy), Hepatitis C, C reactive protein (CRP), Vitamin $B_{12}$, or interferon gamma. For example, the sample region may comprise: (1) a blocking agent, such as bovine serum albumin, skim milk powder, and/or casein; (2) a surfactant, such as polyethylene glycol sorbitan monolaurate (e.g., Tween 20); (3) a buffer, such as phosphate buffered saline, a sodium carbonate buffer, and/or a HEPES buffer; (4) a ligand configured to capture a species to be assayed, such as a monoclonal or a polyclonal antibody, a nanobody, and/or an aptamer (which is optionally conjugated to a species that may be easily detected, such as a colored particle (e.g., a colloidal gold nanoparticle), an enzyme (e.g., horseradish peroxidase), and/or a fluorescent species (e.g., a fluorophore)); and/or (5) a treatment agent and/or a stabilizing agent, such as sucralose, trehalose, and/or albumin. Non-limiting examples of suitable antibodies include anti-pLDH (malaria), anti-p24 (HIV), anti-hCG (pregnancy), anti-CRP (acute phase injury), anti-NS1 (dengue) and anti-human IgG.

In some embodiments, a sample region may comprise one or more reagents suitable for performing an enzymatic assay, such as an enzymatic assay for acetylcholinesterase (e.g., as found on red blood cell membranes) and/or liver enzymes (e.g., alkaline phosphatase, such as as found in plasma). For example, the sample region may comprise: (1) a colorimetric indicator, such as 5,5-dithio-bis-(2-nitrobenzoic acid); (2) an enzymatic substrate, such as acetylthiocholine chloride; and/or (3) a buffer, such as tris buffer.

In some embodiments, a sample region may comprise one or more reagents suitable for performing a blood type analysis. For example, the sample region may comprise: (1) anti-A sera; (2) anti-B sera; and/or (3) anti-D sera.

In some embodiments, a sample region may comprise one or more reagents suitable for detecting one or more types of cells. For example, the sample region may comprise: (1) a ligand configured to capture a species to be assayed, such as a monoclonal or a polyclonal antibody, a nanobody, and/or an aptamer (which is optionally conjugated to a species that may be easily detected, such as a colored particle (e.g., a colloidal gold nanoparticle), an enzyme (e.g., horseradish peroxidase), and/or a fluorescent species (e.g., a fluorophore)); and/or (2) a buffer.

In some embodiments, a sample region may comprise one or more reagents suitable for detecting one or more solutes (e.g., one or more solutes in a fluid sample flowing through the fluidic device), such as one or more species in a metabolite panel (e.g., glucose, total protein level, alkaline phosphatase, creatinine, and/or blood urea nitrogen), DNA, and/or RNA. For example, the sample region may comprise: (1) a denaturant configured to act as a stabilizer, such as sodium dodecylsulfate; (2) silk fibroin; (3) RNAse and/or DNAse; and/or (4) an enzyme inhibitor, such as a protease.

Further examples of reagents that may be stored in the fluidic devices described herein include glucose-6-phosphate dehydrogenase, folate, ATP, and potassium.

Non-limiting examples of fluid samples that may be analyzed in the fluidic devices described herein include fluids of biological origin, such as blood (e.g., whole blood) and fluids derived from blood (e.g., plasma), cerebrospinal fluid, tissue biopsies, and milk.

As an example of an analysis that may be performed on a fluid, in some embodiments, a fluidic device is employed to determine the concentration a species in blood. The species may be a species that is present in plasma and/or may be a species that is present in intact blood cells. For instance, in some embodiments, a fluidic device may be employed to determine the concentration of potassium in blood. Without wishing to be bound by any particular theory, it may be desirable to measure the concentration of potassium in blood in order to monitor electrolytes therein, to diagnose causes of muscle weakness and/or irregular heartbeat, and/or to monitor chronic conditions such as hypertension and/or kidney disorders.

In some embodiments, a fluidic device may comprise one or more regions configured to perform one or more analyses in situ that are not configured to receive a fluid sample from a central region. For example, the fluidic device may comprise a humidity sensor, such as cobalt(II) chloride.

In some embodiments, a fluidic device may comprise one or more features designed to aid identification of the fluidic device and/or one or more samples contained therein. For instance, the fluidic device may comprise a QR code, which may be linked to an online database including one or more types of information, such as information about a patient from which samples on contained on the device have originate and/or information about a hospital and/or clinic used by the patient (and/or at which the fluidic device was used to obtain the samples). In some embodiments, a QR code may be used to improve tracking of the fluidic device.

As described above, fluidic devices described herein may comprise one or more layers. In some embodiments, one or more of the layers of the fluidic device comprises a porous, absorbent material (e.g., one or more layers comprising one or more channels, one or more central regions, and/or one or more sample regions). The porous, absorbent material may, upon exposure to a fluid sample, wick the fluid sample into the layer and/or wick the fluid sample through the layer. When layers comprising channels comprise a porous, absorbent material, the porous, absorbent material may wick the fluid sample into the channels therein and/or through the channels therein. In some embodiments, a fluid may flow into and/or through a porous, absorbent material due to capillarity (capillary action) or by wicking. In some embodiments, a fluid sample may flow into and/or through a porous, absorbent material due to capillarity. In some embodiments, a porous, absorbent material will, upon exposure to a fluid sample (e.g., a fluid sample of interest, a fluid sample for which it is absorbent), transport the fluid sample into the interior of the porous, absorbent material (i.e., the fluid sample may penetrate into the interior of the material in which the pores are positioned, such as into the interior of fibers making up a porous, absorbent material that comprises fibers). In some embodiments, a porous, absorbent material will, upon exposure to a fluid sample, experience an increase in mass due to the fluid sample absorbed therein. It should be understood that some layers comprising porous absorbent materials may have one or more of the properties described above with respect to porous, absorbent materials.

In some embodiments, a fluidic device comprises a porous, absorbent material that is hydrophilic and/or may comprise a layer that is hydrophilic (e.g., a layer comprising a hydrophilic porous, absorbent material). The hydrophilic material or layer may have a water contact angle of less than or equal to 90°, less than or equal to 85°, less than or equal to 80°, less than or equal to 75°, less than or equal to 70°, less than or equal to 65°, less than or equal to 60°, less than or equal to 55°, less than or equal to 50°, less than or equal to 45°, less than or equal to 40°, less than or equal to 35°, less than or equal to 30°, less than or equal to 25°, less than or equal to 20°, less than or equal to 15°, less than or equal to 10°, or less than or equal to 5°. The hydrophilic material or layer may have a water contact angle of greater than or equal to 0°, greater than or equal to 5°, greater than or equal to 10°, greater than or equal to 15°, greater than or equal to 20°, greater than or equal to 25°, greater than or equal to 30°, greater than or equal to 35°, greater than or equal to 40°, greater than or equal to 45°, greater than or equal to 50°, greater than or equal to 55°, greater than or equal to 60°, greater than or equal to 65°, greater than or equal to 70°, greater than or equal to 75°, greater than or equal to 80°, or greater than or equal to 85°. Combinations of the above-referenced ranges are also possible (e.g., less than or equal to 900 and greater than or equal to 0°). Other ranges are also possible. The water contact angle of a hydrophilic material or layer may be measured using ASTM D5946-04, which comprises positioning a water droplet on a planar solid surface of the hydrophilic material or layer. The water contact angle is the angle between the planar solid surface of the hydrophilic material or layer and the tangent line drawn to the water droplet surface at the three-phase point. A contact angle meter or goniometer can be used for this determination. In some embodiments, the hydrophilicity of the hydrophilic material or layer may be such that a water droplet placed on the surface completely wets the surface (e.g., the water droplet is completely absorbed into the material, making the water contact angle 0°). In some embodiments, a device may comprise a porous, absorbent material that is hydrophobic and/or may comprise a layer that is hydrophobic. The hydrophobic material or layer may have a water contact angle outside the ranges described above.

In some embodiments, a porous, absorbent material is a cellulose-based material. The cellulose-based material may comprise cellulose derived from wood (e.g., it may be a wood-based material), cellulose derived from cotton (e.g., it may be a cotton-based material), and/or nitrocellulose.

In some embodiments, a porous, absorbent material comprises a synthetic material and/or a glass. Non-limiting examples of suitable synthetic materials include poly(ether sulfone), polyesters, and nylons.

Porous, absorbent materials described herein may have a variety of designs. In some embodiments, a fluidic device comprises a porous, absorbent material that is a fibrous material (e.g., a fibrous material comprising fibers formed from a cellulose-based material). The fibrous material may be a non-woven material, or may be a woven material. The fibers may have a variety of suitable diameters and distributions of diameters, and, if woven, may be woven in a variety of suitable weaves. In some embodiments, the non-woven material is a paper, such as a cellulose-based paper. A wide variety of commercially available cellulose-based papers may be employed, such as those manufactured by Whatman, those manufactured by Ahlstrom, and/or those manufactured by Munktell.

Fibrous materials may comprise fibers having any suitable average fiber diameter. The average fiber diameter of the fibers may be greater than or equal to 0.1 micron, greater than or equal to 0.2 microns, greater than or equal to 0.5 microns, greater than or equal to 1 micron, greater than or equal to 2 microns, greater than or equal to 5 microns, greater than or equal to 10 microns, greater than or equal to 15 microns, greater than or equal to 20 microns, greater than or equal to 25 microns, greater than or equal to 30 microns, greater than or equal to 40 microns, greater than or equal to 50 microns, greater than or equal to 60 microns, or greater than or equal to 70 microns. The average fiber diameter of the fibers may be less than or equal to 75 microns, less than or equal to 70 microns, less than or equal to 60 microns, less than or equal to 50 microns, less than or equal to 40 microns, less than or equal to 30 microns, less than or equal to 25 microns, less than or equal to 20 microns, less than or equal to 15 microns, less than or equal to 10 microns, less than or equal to 5 microns, less than or equal to 2 microns, less than or equal to 1 micron, less than or equal to 0.5 microns, or less than or equal to 0.2 microns. Combinations of the above-referenced ranges are also possible (e.g., greater than or equal to 0.1 micron and less than or equal to 75 microns). Other ranges are also possible. The average fiber diameter may be determined using electron microscopy.

Porous, absorbent materials and layers comprising porous, absorbent materials described herein may have a variety of suitable porosities. The porosity of a porous, absorbent material and/or a layer comprising a porous, absorbent material may be greater than or equal to 1 vol %, greater than or equal to 2 vol %, greater than or equal to 5 vol %, greater than or equal to 10 vol %, greater than or equal to 20 vol %, greater than or equal to 50 vol %, greater than or equal to 55 vol %, greater than or equal to 60 vol %, greater than or equal to 65 vol %, greater than or equal to 70 vol %, greater than or equal to 75 vol %, or greater than or equal to 80 vol %. The porosity of a porous, absorbent material and/or a layer comprising a porous, absorbent material may be less than or equal to 85 vol %, less than or equal to 80 vol %, less than or equal to 75 vol %, less than or equal to 70 vol %, less than or equal to 65 vol %, less than or equal to 60 vol %, less than or equal to 55 vol %, less than or equal to 50 vol %, less than or equal to 20 vol %, less than or equal to 10 vol %, less than or equal to 5 vol %, or less than or equal to 2 vol %. Combinations of the above-referenced ranges are also possible (e.g., greater than or equal to 1 vol % and less than or equal to 85 vol %, greater than or equal to 1 vol % and less than or equal to 80 vol %, or greater than or equal to 50 vol % and less than or equal to 80 vol %). Other ranges are also possible. The porosity of a material or a layer may be determined by mercury intrusion porosimetry.

Porous, absorbent materials and layers comprising porous, absorbent materials described herein may comprise pores with a variety of suitable sizes. The average pore size of a porous absorbent material and/or a layer comprising a porous, absorbent material may be greater than or equal to 0.1 micron, greater than or equal to 0.2 microns, greater than or equal to 0.5 microns, greater than or equal to 1 micron, greater than or equal to 2 microns, greater than or equal to 5 microns, greater than or equal to 10 microns, greater than or equal to 15 microns, greater than or equal to 20 microns, greater than or equal to 25 microns, greater than or equal to 30 microns, greater than or equal to 35 microns, greater than or equal to 40 microns, greater than or equal to 50 microns, greater than or equal to 75 microns, greater than or equal to 100 microns, or greater than or equal to 125 microns. The average pore size of a porous absorbent material and/or a layer comprising a porous, absorbent material may be less than or equal to 150 microns, less than or equal to 125 microns, less than or equal to 100 microns, less than or equal to 75 microns, less than or equal to 50 microns, less than or equal to 40 microns, less than or equal to 35 microns, less than or equal to 30 microns, less than or equal to 25 microns, less than or equal to 20 microns, less than or equal to 15 microns, less than or equal to 10 microns, less than or equal to 5 microns, less than or equal to 2 microns, less than or equal to 1 micron, less than or equal to 0.5 microns, or less than or equal to 0.2 microns. Combinations of the above-referenced ranges are also possible (e.g., greater than or equal to 0.1 micron and less than or equal to 150 microns, or greater than or equal to 2 microns and less than or equal to 40 microns). Other ranges are also possible. The average pore size of a porous, absorbent material or a layer comprising a porous, absorbent material may be determined by mercury intrusion porosimetry.

As described above, layers comprising porous, absorbent materials may also comprise one or more regions and/or channels. For instance, layers comprising porous, absorbent materials may also comprise a central region in fluidic communication with an environment external to a fluidic device (e.g., a central region configured to receive a fluid sample from the environment external to the fluidic device), one or more channels, and/or one or more sample regions. In some embodiments, the central region, the one or more channels, and/or the one or more sample regions may be positioned in the porous, absorbent material. Regions and/or channels may be formed in a layer and/or material (e.g., a layer comprising a porous, absorbent material and/or a porous, absorbent material) by a variety of suitable methods. By way of example, a barrier impermeable to a fluid may be infiltrated into portions of the layer and/or material to define channels and/or regions therein. This may be accomplished by, e.g., printing (e.g., wax printing, 3D-printing) and/or pattern transfer methods (e.g., by use of photoresists and/or UV-curable materials). The fluid to which the barrier is impermeable (e.g., a fluid sample, one or more components of a fluid sample) may, upon entering a channel and/or region defined by an impermeable barrier, be confined to portions of the layer and/or material of which it can flow through without crossing the impermeable barrier (e.g., channels and/or regions in fluidic communication with the channel and/or region defined by the impermeable barrier).

Barriers impermeable to a variety of fluids may be employed. In some embodiments, the fluid to which a barrier is impermeable is an aqueous fluid, such as a fluid of biological origin. Non-limiting examples of fluids of biological origin include blood (e.g., whole blood) and fluids derived from blood (e.g., plasma), cerebrospinal fluid, tissue biopsies, and milk. The barrier impermeable to a fluid may comprise a variety of suitable materials, non-limiting examples of which include waxes, polymers, and hydrophobic materials (e.g., hydrophobic waxes, hydrophobic polymers, other hydrophobic materials).

As described above, fluidic devices described herein may comprise filtration layers. In some embodiments, a filtration layer is configured to filter blood cells from blood. The filtration layer may be configured to retain greater than or equal to 80%, greater than or equal to 85%, greater than or equal to 90%, greater than or equal to 95%, greater than or equal to 97%, greater than or equal to 99%, greater than or equal to 99.5%, or greater than or equal to 99.9% of the blood cells in blood that it filters. The filtration layer may be configured to retain less than or equal to 100%, less than or equal to 99.9%, less than or equal to 99.5%, less than or equal to 99%, less than or equal to 97%, less than or equal to 95%, less than or equal to 90%, or less than or equal to 85% of the blood cells in blood that it filters. Combinations of the above-referenced ranges are also possible (e.g., greater than or equal to 80% and less than or equal to 100%, or greater than or equal to 90% and less than or equal to 100%). Other ranges are also possible. Some methods may comprise passing blood through a filtration layer, and it should be understood that these methods may comprise retaining a percentage of blood cells in one or more of the ranges described above on a first side of the filtration layer (e.g., a side adjacent an environment external to the fluidic device). The percentage of blood cells retained by the filtration layer may be determined by: (1) measuring the number of blood cells in a blood sample; (2) passing the blood sample through the filtration layer; (3) measuring the number of blood cells in the blood sample after passage through the filtration layer; (4) calculating a ratio of the number of blood cells in the blood sample after passage through the filtration layer to the number of blood cells in the blood sample prior to passage through the filtration layer; and (5) calculating the percentage of blood cells retained by the filtration layer based on the ratio calculated in step (4).

In some embodiments, a fluidic device comprises a filtration layer configured to filter certain types of blood cells from blood. The filtration layer may be configured to pass some types of cells therethrough, and/or may be configured to also filter out other types of cells. For instance, some filtration layers may be configured to retain white blood cells from blood while passing red blood cells and platelets therethrough (or vice versa). It should be understood that the ranges described above may refer to the percentage of the total number of blood cells retained by the filtration layer or may refer to the percentage of any specific type of blood cells retained by the filtration layer (e.g., the percentage of white blood cells retained by the filtration layer, the percentage of red blood cells retained by the filtration layer).

In some embodiments, a filtration layer is configured to pass plasma in blood therethrough. The filtration layer may be configured to pass at least 20%, at least 30%, at least 40%, at least 50%, at least 60%, at least 65%, at least 70%, at least 75%, at least 80%, at least 85%, at least 90%, at least 95%, at least 97%, at least 99%, or at least 99.9% of the plasma in blood that it filters therethrough. The filtration layer may be configured to pass at most 100%, at most 99.9%, at most 99%, at most 97%, at most 95%, at most 90%, at most 85%, at most 80%, at most 75%, at most 70%, at most 65%, at most 60%, at most 50%, at most 40%, or at most 30% of the plasma in blood that it filters therethrough. Combinations of the above-referenced ranges are also possible (e.g., at least 20% and at most 100%, at least 20% and at most 80%, or at least 60% and at most 80%). Other ranges are also possible. In some embodiments, the filtration layer may pass all of the plasma in the blood therethrough, or all of the plasma in the blood except for a minimal percentage of the plasma in the blood therethrough. Some methods may comprise passing blood through a filtration layer, and it should be understood that these methods may comprise transporting a percentage of plasma in one or more of the ranges described through the filtration layer and/or away from the filtration layer (e.g., through a channel in a layer positioned beneath the filtration layer). The percentage of plasma passed through the filtration layer may be determined from information provided by a commercial supplier of the filtration layer. If the commercial supplier of the filtration layer does not provide this information, it may be determined by: (1) measuring the volume of a plasma sample; (2) passing the plasma sample through the filtration layer; (3) measuring the volume of the plasma sample after passage through the filtration layer; (4) dividing the volume of the plasma sample after passage through the filtration layer by the volume of a plasma sample prior to passage through the filtration layer; and (5) multiplying by 100%.

In some embodiments, a filtration layer is configured to lyse at least a portion of blood cells in blood samples that it filters. In some embodiments, a layer disposed on a filtration layer is configured to lyse at least a portion of blood cells in a blood sample prior to exposure of the blood sample to the filtration layer (e.g., as part of a sample preparation layer). The filtration layer and/or layer disposed on the filtration layer may comprise a lysis reagent, such as saponin. The blood may be react with the lysis reagent as it passes through the filtration layer and/or layer disposed on the filtration layer and become at least partially lysed. The filtration layer and/or layer disposed on the filtration layer may be configured to lyse less than or equal to 100%, less than or equal to 75%, less than or equal to 50%, less than or equal to 40%, less than or equal to 30%, less than or equal to 20%, less than or equal to 10%, less than or equal to 5%, less than or equal to 2%, or less than or equal to 1% of the blood cells in a blood sample passing therethrough. The filtration layer and/or layer disposed on the filtration layer may be configured to lyse greater than or equal to 0%, greater than or equal to 1%, greater than or equal to 2%, greater than or equal to 5%, greater than or equal to 10%, greater than or equal to 20%, greater than or equal to 30%, greater than or equal to 40%, greater than or equal to 50%, or greater than or equal to 75% of the blood cells in a blood sample passing therethrough. Combinations of the above-referenced ranges are also possible (e.g., less than or equal to 50% and greater than or equal to 0%, or less than or equal to 100% and greater than or equal to 1%). Other ranges are also possible.

In some embodiments, a fluidic device comprises a filtration layer that is hydrophilic. The filtration layer may have a water contact angle of less than or equal to 90°, less than or equal to 85°, less than or equal to 80°, less than or equal to 75°, less than or equal to 70°, less than or equal to 65°, less than or equal to 60°, less than or equal to 55°, less than or equal to 50°, less than or equal to 45°, less than or equal to 40°, less than or equal to 35°, less than or equal to 30°, less than or equal to 25°, less than or equal to 20°, less than or equal to 15°, less than or equal to 10°, or less than or equal to 5°. The filtration layer may have a water contact angle of greater than or equal to 0°, greater than or equal to 5°, greater than or equal to 10°, greater than or equal to 15°, greater than or equal to 20°, greater than or equal to 25°, greater than or equal to 30°, greater than or equal to 35°, greater than or equal to 40°, greater than or equal to 45°, greater than or equal to 50°, greater than or equal to 55°, greater than or equal to 60°, greater than or equal to 65°, greater than or equal to 70°, greater than or equal to 75°, greater than or equal to 80°, or greater than or equal to 85°. Combinations of the above-referenced ranges are also possible (e.g., less than or equal to 900 and greater than or equal to 0°). Other ranges are also possible. The water contact angle of a filtration layer may be measured using ASTM D5946-04, which comprises positioning a water droplet on a planar solid surface of the filtration layer. The water contact angle is the angle between the planar solid surface of the filtration layer and the tangent line drawn to the water droplet surface at the three-phase point. A contact angle meter or goniometer can be used for this determination. In some embodiments, the hydrophilicity of the filtration layer may be such that a water droplet placed on the surface completely wets the surface (e.g., the water droplet is completely absorbed into the material making the water contact angle 0°). In some embodiments, a device may comprise a filtration layer that is hydrophobic. The hydrophobic filtration layer may have a water contact angle outside the ranges described above.

Filtration layers may comprise a variety of suitable materials. In some embodiments, a filtration layer comprises a synthetic material, such as a polymer. Non-limiting examples of suitable polymers include nylons, polyesters, and poly(ether sulfone). In some embodiments, a filtration layer comprises a glass. In some embodiments, a filtration layer comprises a hydrophilic material (e.g., a hydrophilic polymer).

In some embodiments, a filtration layer comprises a cellulose-based material. The cellulose-based material may comprise cellulose derived from wood (e.g., it may be a wood-based material, including hardwood fibers and/or softwood fibers), cellulose derived from cotton (e.g., it may be a cotton-based material), and/or nitrocellulose.

Filtration layers described herein may have a variety of designs. In some embodiments, a fluidic device comprises a filtration layer that is a fibrous material (e.g., a fibrous material comprising fibers formed from one or more of the materials described above). The fibrous material may be a non-woven material, or may be a woven material. The fibers may have a variety of suitable diameters and distributions of diameters, and, if woven, may be woven in a variety of suitable weaves. In some embodiments, the filtration layer is a mesh. A wide variety of commercial filters may be employed as filtration layers, such as those manufactured by Pall (e.g., the Vivid Plasma Separation Membrane).

In some embodiments, a fluidic device comprises a filtration layer that is porous. Filtration layers that are porous may have a variety of suitable porosities. The porosity of a porous filtration layer may be greater than or equal to 1 vol %, greater than or equal to 2 vol %, greater than or equal to 5 vol %, greater than or equal to 10 vol %, greater than or equal to 20 vol %, greater than or equal to 50 vol %, greater than or equal to 55 vol %, greater than or equal to 60 vol %, greater than or equal to 65 vol %, greater than or equal to 70 vol %, greater than or equal to 75 vol %, or greater than or equal to 80 vol %. The porosity of a porous filtration layer may be less than or equal to 85 vol %, less than or equal to 80 vol %, less than or equal to 75 vol %, less than or equal to 70 vol %, less than or equal to 65 vol %, less than or equal to 60 vol %, less than or equal to 55 vol %, less than or equal to 50 vol %, less than or equal to 20 vol %, less than or equal to 10 vol %, less than or equal to 5 vol %, or less than or equal to 2 vol %. Combinations of the above-referenced ranges are also possible (e.g., greater than or equal to 1 vol % and less than or equal to 85 vol %, greater than or equal to 1 vol % and less than or equal to 80 vol %, or greater than or equal to 50 vol % and less than or equal to 80 vol %). Other ranges are also possible. The porosity of a porous filtration layer may be determined by mercury intrusion porosimetry.

Filtration layers that are porous may comprise pores with a variety of suitable sizes. The average pore size of a porous filtration layer may be greater than or equal to 0.1 micron, greater than or equal to 0.2 microns, greater than or equal to 0.5 microns, greater than or equal to 1 micron, greater than or equal to 2 microns, greater than or equal to 5 microns, greater than or equal to 10 microns, greater than or equal to 20 microns, greater than or equal to 50 microns, or greater than or equal to 200 microns. The average pore size of a porous filtration layer may be less than or equal to 500 microns, less than or equal to 200 microns, less than or equal to 50 microns, less than or equal to 20 microns, less than or equal to 10 microns, less than or equal to 5 microns, less than or equal to 2 microns, less than or equal to 1 micron, less than or equal to 0.5 microns, or less than or equal to 0.2 microns. Combinations of the above-referenced ranges are also possible (e.g., greater than or equal to 0.1 micron and less than or equal to 500 microns, or greater than or equal to 0.1 micron and less than or equal to 5 microns). Other ranges are also possible. The average pore size of a filtration layer may be determined by mercury intrusion porosimetry.

Filtration layers that are porous may comprise pores with a variety of suitable shapes. In some embodiments, a filtration layer comprises asymmetric pores. The asymmetric pores may have a diameter that varies across the filtration layer. The asymmetric pores may have a larger diameter on a first side of the filtration layer (e.g., a side adjacent to an environment external to the fluidic device, a side configured to receive a fluid sample from an environment external to the fluidic device) and a smaller diameter on a second side of the filtration layer (e.g., a side opposite the first side, a side adjacent to a porous, absorbent layer, a side adjacent to a layer comprising one or more channels and/or one or more sample regions). A filtration layer may comprise pores with a ratio of largest diameter (e.g., diameter of the portion of the pore adjacent to a first side of the filtration layer) to smallest diameter (e.g., diameter of the portion of the pore adjacent to the opposite side of the filtration layer) of greater than or equal to 1:1, greater than or equal to 1.1:1, greater than or equal to 1.2:1, greater than or equal to 1.5:1, greater than or equal to 2:1, greater than or equal to 2.2:1, greater than or equal to 2.5:1, greater than or equal to 3:1, or greater than or equal to 4:1. A filtration layer may comprise pores with a ratio of largest diameter to smallest diameter of less than or equal to 5:1, less than or equal to 4:1, less than or equal to 3:1, less than or equal to 2.5:1, less than or equal to 2.2:1, less than or equal to 2:1, less than or equal to 1.5:1, less than or equal to 1.2:1, or less than or equal to 1.1:1. Combinations of the above-referenced ranges are also possible (e.g., greater than or equal to 1:1 and less than or equal to 5:1). Other ranges are also possible. The variation in pore diameter across a pore may be determined by electron microscopy.

As described above, fluidic devices described herein may comprise one or more layers configured to distribute fluid within the fluidic device. In some embodiments, a fluidic device comprises a layer configured to distribute fluid within the fluidic device that is hydrophilic. The layer configured to distribute fluid within the fluidic device may have a water contact angle of less than or equal to 90°, less than or equal to 85°, less than or equal to 80°, less than or equal to 75°, less than or equal to 70°, less than or equal to 65°, less than or equal to 60°, less than or equal to 55°, less than or equal to 50°, less than or equal to 45°, less than or equal to 40°, less than or equal to 35°, less than or equal to 30°, less than or equal to 25°, less than or equal to 20°, less than or equal to 15°, less than or equal to 10°, or less than or equal to 5°. The layer configured to distribute fluid within the fluidic device may have a water contact angle of greater than or equal to 0°, greater than or equal to 5°, greater than or equal to 10°, greater than or equal to 15°, greater than or equal to 20°, greater than or equal to 25°, greater than or equal to 30°, greater than or equal to 35°, greater than or equal to 40°, greater than or equal to 45°, greater than or equal to 50°, greater than or equal to 55°, greater than or equal to 60°, greater than or equal to 65°, greater than or equal to 70°, greater than or equal to 75° greater than or equal to 80°, or greater than or equal to 85°. Combinations of the above-referenced ranges are also possible (e.g., less than or equal to 900 and greater than or equal to 0°). Other ranges are also possible. The water contact angle of a layer configured to distribute fluid within the fluidic device may be measured using ASTM D5946-04, which comprises positioning a water droplet on a planar solid surface of the layer configured to distribute fluid within the fluidic device. The water contact angle is the angle between the planar solid surface of the layer configured to distribute fluid within the fluidic device and the tangent line drawn to the water droplet surface at the three-phase point. A contact angle meter or goniometer can be used for this determination. In some embodiments, the hydrophilicity of the layer configured to distribute fluid within the fluidic device may be such that a water droplet placed on the surface completely wets the surface (e.g., the water droplet is completely absorbed into the material making the water contact angle 0°).

Layer(s) configured to distribute fluid within the fluidic device may comprise a variety of suitable materials. In some embodiments, a layer configured to distribute fluid within the fluidic device may comprise a synthetic material, such as a polymer. Non-limiting examples of suitable polymers include rayon, PVDF, PLA (e.g., PLA manufactured by Ingeo), polycarbonates, polyesters, nylons, poly(ether sulfone), and blends thereof. In some embodiments, the synthetic material may be a synthetic material that has been treated to increase its hydrophilicity. For instance, a layer configured to distribute fluid within the fluidic device may comprise PVDF that has been treated with methanol to increase its hydrophilicity.

The cover layers described herein typically comprise materials that are relatively impermeable to a variety of fluids (e.g., aqueous fluids), relatively impermeable to a variety of gases (e.g., gases in the ambient environment), and/or relatively scuff and/or abrasion resistant. In some embodiments, a fluidic device comprises a cover layer that is a laminating sheet (such as a Fellowes laminating sheet) and/or an adhesive film. When laminating sheets and/or adhesive films are employed, the fluidic device may be assembled by laminating the other layers thereof (e.g., layers comprising channels, layers comprising central regions, layers comprising sample regions, filtration layers, layers configured to distribute fluid) in between two laminating sheets and/or adhesive films.

Wick pad(s) typically comprise relatively thick, absorbent materials. In some embodiments, a fluidic device comprises a wick pad that is a non-woven material, such as a paper.

The fluidic devices described herein may have one or more features of the fluidic devices described in the U.S. Provisional Application entitled "Fluidic Devices Involving Signal Generation at Converging Liquid Fronts", filed on Jun. 22, 2018, incorporated herein by reference in its entirety. The fluidic devices described herein may have one or more features of the fluidic devices described in the International Patent Application entitled "Fluidic Devices Involving Signal Generation at Converging Liquid Fronts", filed on even date herewith, incorporated herein by reference in its entirety. The fluidic devices described herein may have one or more features of the fluidic devices described in International Patent Publication No. WO 2017/123668, filed on Jul. 20, 2017, and entitled "Separation of Cells Based on Size and Affinity Using Paper Microfluidic Device", incorporated herein by reference in its entirety.

The following examples are intended to illustrate certain embodiments of the present invention, but do not exemplify the full scope of the invention.

Example 1

This Example relates to fluidic devices that are patterned dried blood spot (pDBS) cards. The patterning enhances the overall performance of DBS cards and expands the suite of their potential application in field settings. By patterning paper with hydrophobic barriers, it was possible to regulate sample application, separation, volume, and composition with a high degree of control. Moreover, the pDBS described in this Example enable the integration of blood storage with blood analysis directly onto the fluidic device. These assays—selected from, for example, any combination of immunoassay, blood typing, and measurement of the hematocrit—may provide a snapshot of a patient's health status at the time blood is collected. This capability may be especially advantageous for accommodating the needs of clinical end users.

One example of a pDBS card (shown in FIGS. 4A-4B) is a pDBS card configured to perform HIV viral load analysis on plasma. FIG. 4A shows a schematic diagram and FIG. 4B is a photograph showing a pDBS card. Viral load analyses performed on purified plasma may be more indicative of a patient's health than viral load analyses performed on whole blood or on other samples derived from whole blood. In the fluidic device shown in FIG. 4, whole blood may be added to the sample application zone above a filtration layer, which in this case is a plasma separation membrane (PSM). Below the PSM is a single channel with two sample zones for duplicate plasma regions. Viral load may be determined directly from punches acquired from the plasma zones, while intact blood cells may be enriched and retained in the PSM. Samples punched from the central PSM zone may be analyzed for cellular DNA and protein levels.

Figure 5A:
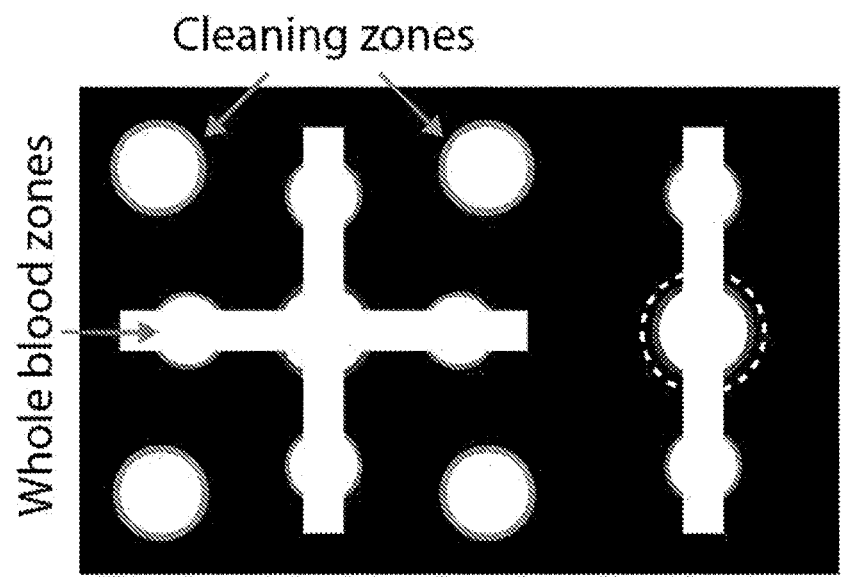
FIG. 5A shows a schematic depiction of a pDBS card, according to some embodiments.
Figure 5B:
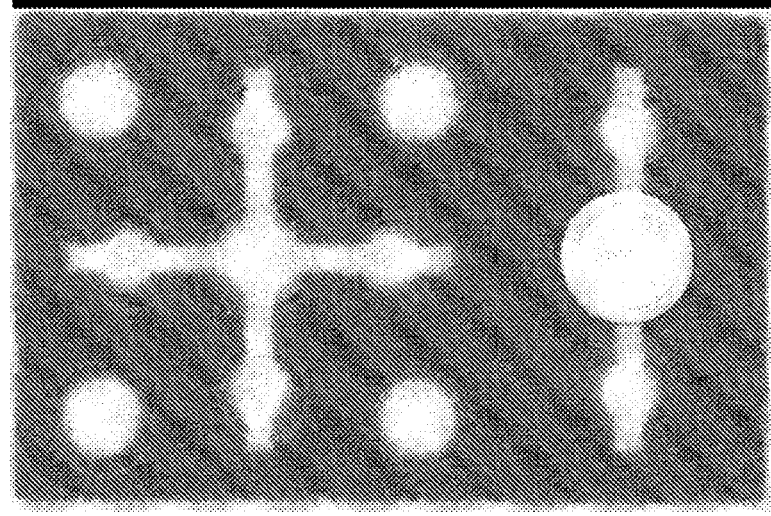
FIG. 5B shows a photograph of a pDBS card, according to some embodiments.

Another example of a pDBS card (shown in FIGS. 5A-5B) is a duplex assay card for simultaneous plasma separation and whole blood storage. FIG. 5A shows a schematic diagram and FIG. 5B is a photograph showing a pDBS card. This pDBS card may lack a filtration layer, and so whole blood flowing into the pDBS card may not be filtered. The whole blood may flow into and ultimately be contained in channels. In the pDBS card shown in FIG. 5, the channels may extend beyond sample regions. Channels with this design may which may allow blood to flow into and past the sample regions, which may promote full saturation of the sample regions. The blank zones surrounding the sample regions may be employed as a cleaning surface for punches between extractions. The pDBS card shown in FIG. 5 may improve the quality and reproducibility of the samples formed thereon in a variety of ways. For example, channels and/or sample regions of known volumes may promote consistent sample distribution and/or volume. As another example, splitting a single sample into multiple channels and output zones may result in the formation of two or more homogenous replicates of the sample. These replicates may be easy to identify and/or remove from the pDBS card if colored circles marking boundaries of the sample regions are also present.

Figure 6A:
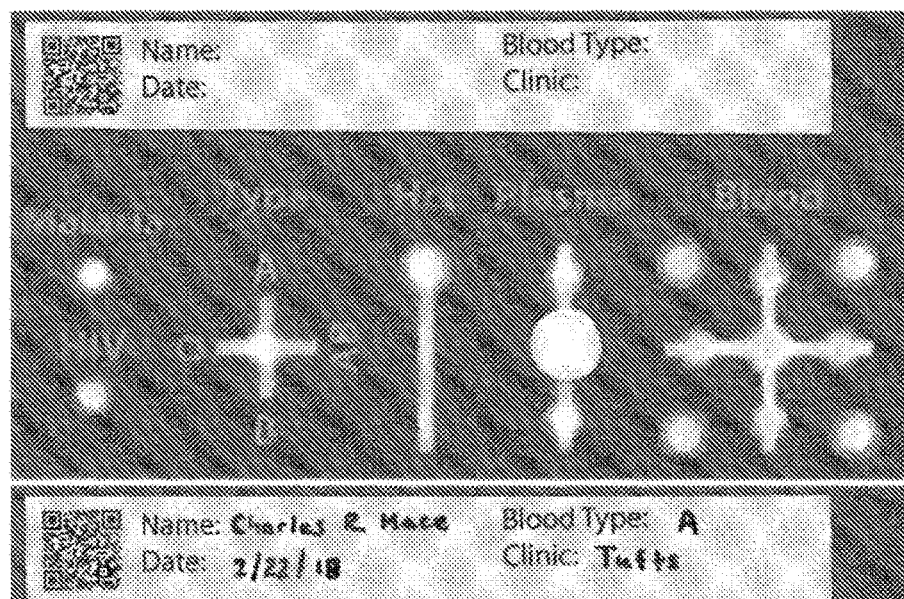
FIGS. 6A-6B are photographs of a pDBS card, according to some embodiments.
Figure 6B:
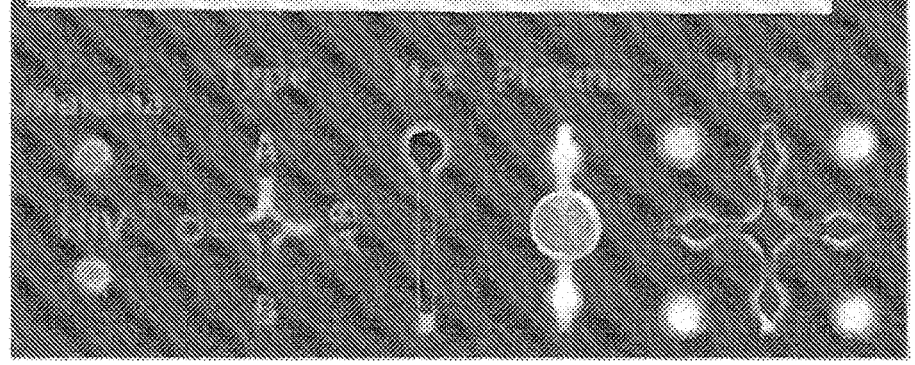

A third example of a pDBS card is shown in FIGS. 6A-6B. FIGS. 6A and 6B are photographs showing a pDBS card. The pDBS card shown in FIGS. 6A-6B may serve as an active sensing platform for field diagnostic applications. This pDBS card is capable of performing hematological assays at the point-of-care. It is configured to perform a variety of analyses on the card, including malaria and HIV immunoassays. The pDBS card shown in FIGS. 6A-6B is also configured to separate and store a patient's plasma, cells, and blood, and to provide a snapshot of the their overall health status.

Figure 7:
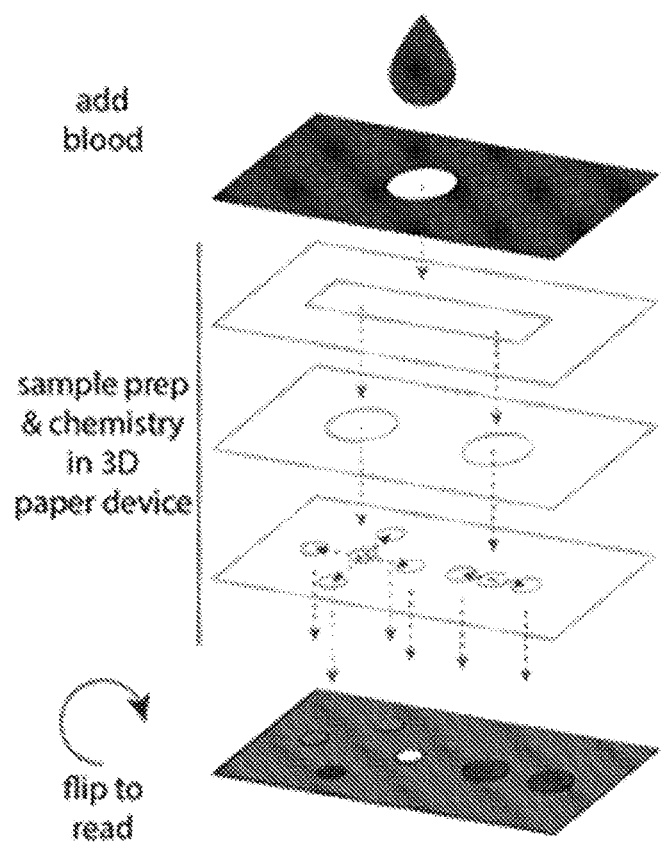
FIG. 7 shows a schematic diagram of a pDBS card, according to some embodiments.

A fourth example of a pDBS card is shown in FIG. 7. FIG. 7 shows a schematic diagram of a pDBS card. The pDBS card shown in FIG. 7 is a three-dimensional pDBS which is configured to split a single drop of blood between a plurality of patterned channels in order to direct blood to stabilization, preparation, and/or assay zones. In one embodiment, the tests are visualized by flipping the pDBS card to inspect the back. In another embodiment, layers of the device may be peeled away to reveal an assay spot or multitude of assay spots. In another embodiment, different areas of the pDBS card may be removed to test different components of the blood sample that has been separated, prepared, or reacted on the pDBS card.

Example 2

Figure 8:
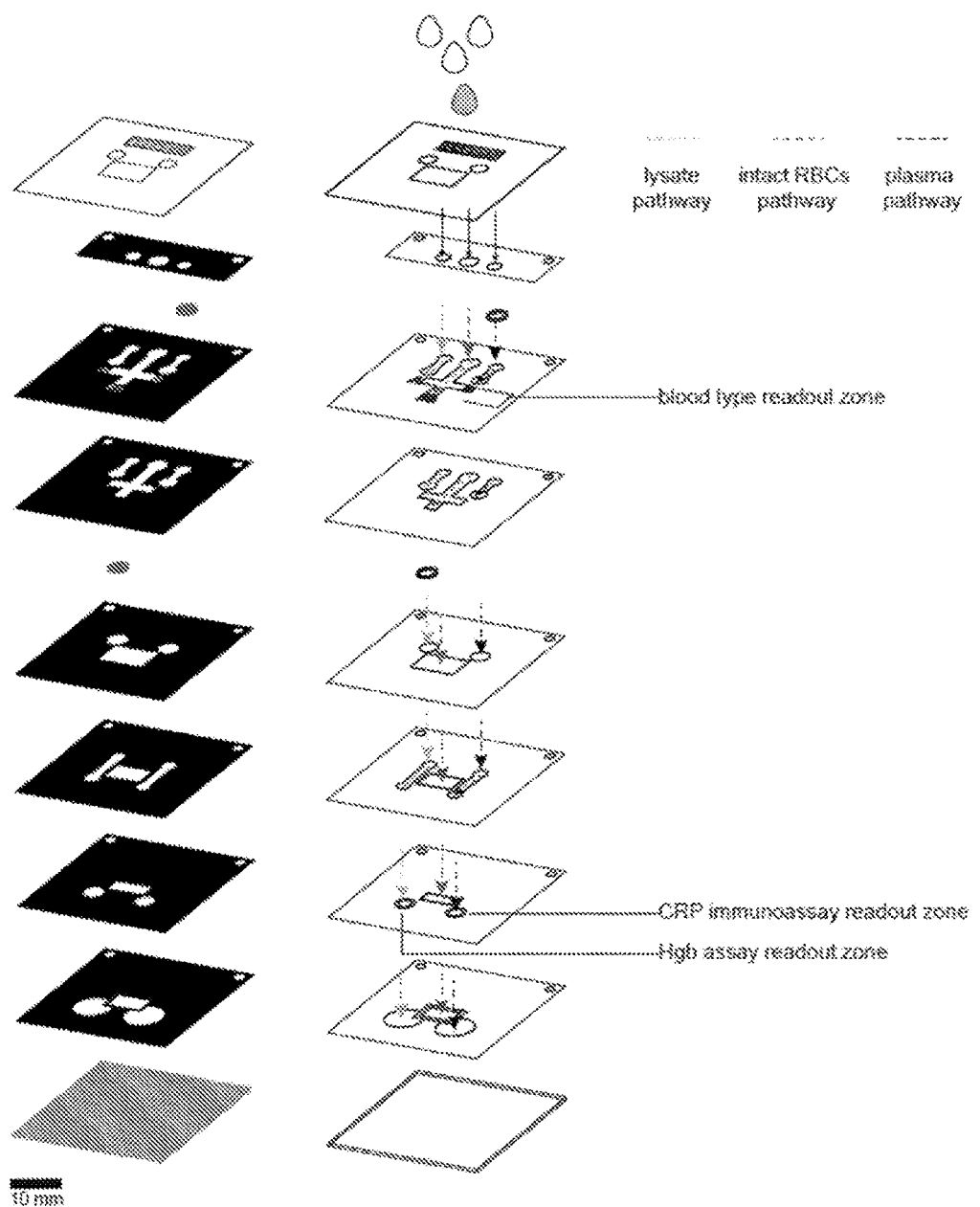
FIG. 8 shows a schematic depiction of a multilayer fluidic device according to some embodiments.

This Example describes the design and use of a multilayer fluidic device. This multilayered device, shown schematically in FIG. 8, is designed to take a single sample of blood (gray droplet) and split it among three separate channels in order to perform analyses on intact blood cells (e.g., blood typing), lysed blood cells (e.g., hemoglobin), and plasma (e.g., C-reactive protein) that has been purified of any cellular matter. After blood has been added, aliquots of wash buffer or reagents (white droplets) can be added to exposed areas of the assembled device to complete assays. Upon addition of these buffers and waiting an appropriate time for reaction, the device can be read. Some assays may be read directly on top of the device (e.g., blood typing), while others are read after the device is peeled to expose internal layers (e.g., hemoglobin and CRP at layer 9).

The entire device comprises a total of 11 layers of porous, absorbent materials (referred to below as paper layers), layers that are configured to distribute fluid (referred to below as porous membranes), or cover layers. In between each layer (and not shown) are double-sided adhesives that affix layers to each other. The narrative below describes the structure of each layer and how it is designed to interact with fluid samples introduced to the fluidic device.

Layer 1. A cover layer that is an adhesive film with four cut-outs (e.g., regions in fluidic communication with an environment external to the fluidic device). One cut-out (hash) is used to affix a porous polymer mesh that distributes applied blood to the zones in the porous, absorbent layer (e.g., paper layer) below. The other three cut-outs expose wash or reagent application zones in the paper layer below.

Layer 2. A paper layer with three zones that take a blood sample from the mesh layer above. Lysis reagent can be stored in the leftmost zone.

Layer 3. A layer configured to distribute fluid (e.g., a porous polymer-based membrane comprising poly (ether sulfone)) that separates blood cells from plasma. This material is affixed only to the third set of channels for the plasma pathway (black lines; rightmost).

Layers 4/5. Two layers of paper with identical patterns, which are used to speed up the transport of intact and lysed blood cells. Lysis reagent can be stored in the leftmost zone. Lysed blood cells (light gray lines; leftmost) are directed to a straight channel. Intact blood cells (dark gray lines; center)

are directed to another channel. In this fluidic device, this single channel splits into three new channels, one each for the detection of various antigens in blood typing (i.e., A, B, Rh).

Layer 6. A porous polymer-based membrane that separates blood cell particles from hemolysate (e.g., poly(ether sulfone)). This material is affixed only to the first set of channels for the lysate pathway.

Layer 7. A paper layer that can be used to store reagents. The leftmost zone (lysate channel) contains reagents to detect hemoglobin in lysed red blood cells as a model example of an assay for analytes in hemolysate. The center rectangle (intact channel) is for wicking only (i.e., it does not contain any reagents). The rightmost zone (plasma channel) contains reagents for a C-reactive protein immunoassay as a model example of an assay for analytes in plasma.

Layer 8. A paper layer that can be used to mix sample and reagents and control the time of an assay. The leftmost and rightmost channel lengths and widths control these parameters. The center rectangle (intact channel) is for wicking only.

Layer 9. A paper and/or porous membrane layer (e.g., nylon) that can be used to read out the results of an assay via reagent or product capture. The leftmost and rightmost channels are used for these purposes. The center rectangle (intact channel) is for wicking only.

Layer 10. A paper layer that is used to collect excess sample, reagent, or wash solution.

Layer 11. A paper layer that is used to collect excess sample, reagent, or wash solution.

Figure 9A:
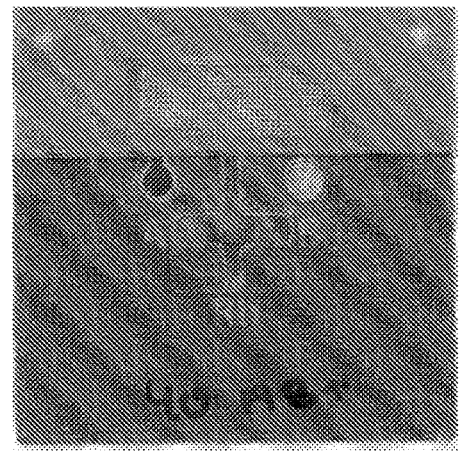
FIGS. 9A-9B show photographs of fluidic devices having the structure shown in FIG. 8 that have been employed to analyze blood samples, according to some embodiments.
Figure 9B:
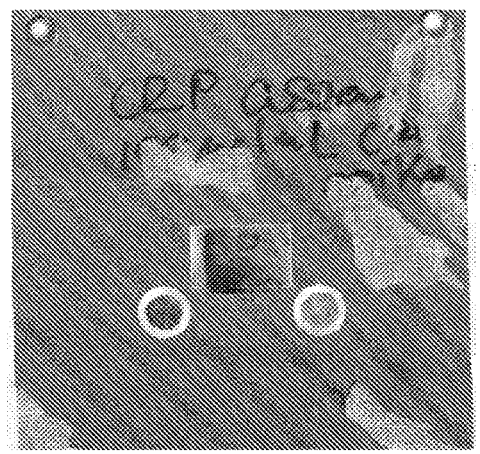

A fluidic device with the structure described above was employed to perform an analysis on a blood sample. The results from this analysis are shown in FIGS. 9A and 9B. The blood sample had a normal hematocrit (40%) and was of AB+ blood type. FIG. 9A shows a user view of the top four layers of the device. The mesh (layer 1) and sample transport/readout (layer 4) are visible; the sample splitting layer (layer 2) is slightly visible below the blood impregnated mesh; the plasma separation membrane (layer 3) cannot be seen.

The left spot in FIG. 9A shows blood that has been transported to a lysis zone. It appears as a dark red spot.

The center cross sign in FIG. 9A shows blood that has been transported to three channels impregnated with blood-typing antibodies to A/B/Rh blood antigens. In this case, the blood is positive for all three antigens, which causes them to agglutinate, block paper channels, and remain in the paper after the addition of a wash buffer. An O− blood type, alternatively, would cause all three channels to remain colorless due to removal of unreacted blood cells.

The right spot in FIG. 9A shows plasma that has been purified of all blood cells. It appears yellowish.

FIG. 9B shows a user view of the 9th layer after the layers 1-8 device have been peeled to expose layers 9-11.

The left spot in FIG. 9B shows blood that has been successfully lysed, and so appears as a dark red spot. If no lysis occurred, due to the plasma separation membrane on layer 6, then yellow plasma would be apparent. Although not present in the fluidic device shown in FIGS. 8 and 9A-9B, in some embodiments, hemoglobin assay reagents may be present in this channel in some fluidic devices.

The center square in FIG. 9B shows a wash layer for blood cells that did not react with stored antibodies for the blood typing assay.

The right spot in FIG. 9B shows blood that has tested positive for CRP. Blood lacking CRP or including an amount of CRP below a threshold concentration would show a clean white spot.

Example 3

This Example describes the design of a fluidic device comprising configured to lyse at least a portion of blood cells in blood samples that it analyzes.

It may be desirable to lyse red blood cells (RBCs) to measure Hgb. When lysis is performed prior to initiating an assay, it may result in increased cost and complexity. Lysis performed in-line and/or as an intrinsic component of a measurement may be beneficial. The fluidic device may comprise a layer (e.g., a top layer) in which a lysis reagent, such as saponin, is stored. As a blood sample flows through the layer comprising the lysis reagent, it may rehydrate the lysis reagent. Upon rehydration of saponin by the blood sample, RBCs in the blood sample may be preferentially lysed and/or may release intraerythrocytic species (e.g., Hgb, malaria antigens, folic acid, glucose-6-phosphate dehydrogenase) into layers of the fluidic device positioned below the layer comprising the lysis reagent. A material that prohibits or substantially reduces the transport of intact RBCs and/or fragments (e.g., plasma separation membrane, a filtration layer) may be positioned below the layer comprising the lysis reagent. This material may cause only hemolysate (or hemolysate including very few impurities) to be present for subsequent colorimetric analysis. The concentration and efficacy of the stored reagent may be employed to control the extent of lysis. Hemolysate prepared off-chip may serve as a control for complete lysis to enable comparisons among conditions.

Figure 10:
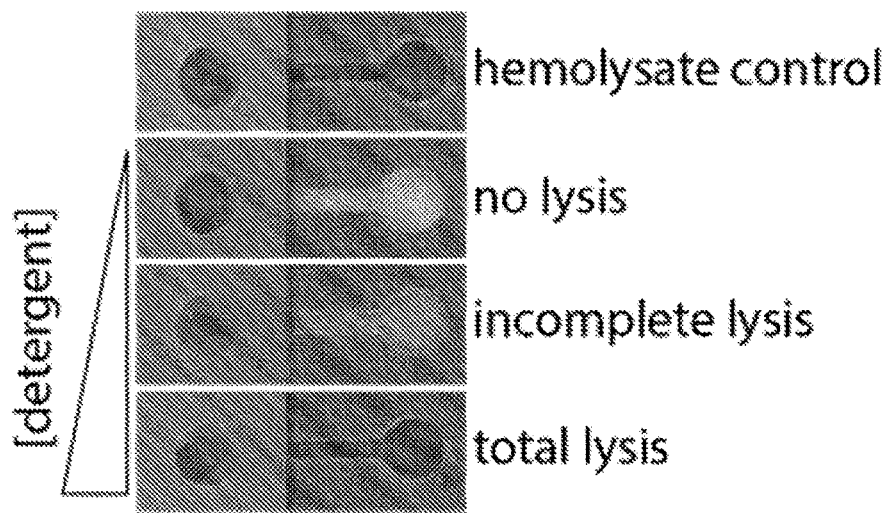
FIG. 10 shows photographs of a fluidic device comprising a layer comprising saponin which has been used to analyze a blood sample, according to some embodiments.

FIG. 10 shows an exemplary fluidic device comprising a layer comprising saponin which has been used to analyze a blood sample. Whole blood was added to a layer that comprised saponin-treated paper. This layer lysed the RBCs in the blood sample. A filtration layer positioned below the layer comprising saponin removed RBC fragments. Soluble Hgb was transported to the end of a channel, which marked the extent of lysis.

Example 4

This Example describes a fluidic device configured to lyse blood samples and perform analysis of red blood cells in blood samples.

Figure 11:
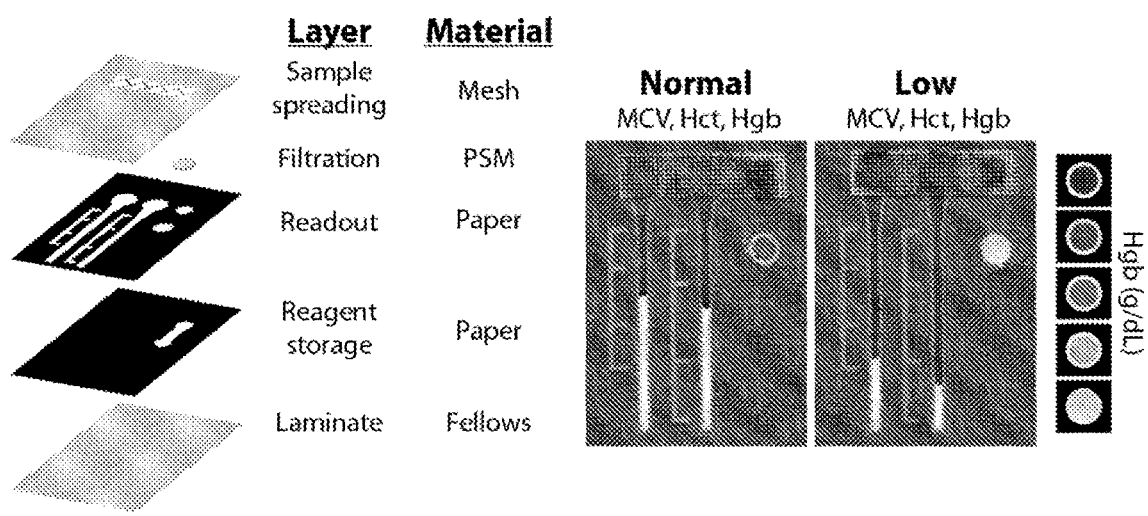
FIG. 11 shows a schematic depiction and photographs of a fluidic device configured to lyse and analyze blood samples, according to some embodiments.

Integrated fluidic devices for whole cell analysis and in-line lysis of RBCs may be developed by following three dedicated steps: (i) Equivalence may be established between measurements of the Hct and MCV made by singleplex devices and multichannel devices. RBCs spanning a range of MCVs (50-175 fL) may be introduced to the fluidic devices at concentrations that also correspond to a range of Hct expected in anemias and in healthy patients (30-55%). Clinical samples of whole blood may be characterized with a CBC, which may allow for a post-hoc analysis of the previous data set in addition to evaluating a new set of samples of whole blood. (ii) Hemolysate prepared on- and off-chip using whole blood acquired from healthy donors may be compared to each other to quantify Hgb. A single, large volume of donor blood may permit characterization using standard methods. (iii) Assays for Hct, MCV, and Hgb may be combined onto a single paper-based microfluidic device that share a common sample application layer including a layer configured to distribute fluid (e.g., a porous, polymer membrane) that results in minimal sample loss (FIG. 11). Device modifications (e.g., selection of hydrophilic, porous materials) helpful for integrating the three assays may be employed. Equivalence tests may be employed to evaluate the extent of agreement between each assay performed in singleplex and multiplex. Blood may be applied to the fluidic device by addition of a single droplet to a common sample splitting layer. The fluidic device may be designed to self-meter the desired volumes to each measurement channel. The multiplex fluidic device may require less than 100 µL of blood to complete all assays.

Example 5

This Example describes the design and fabrication of a multilayer fluidic device that is also a pDBS card.

Figure 12:
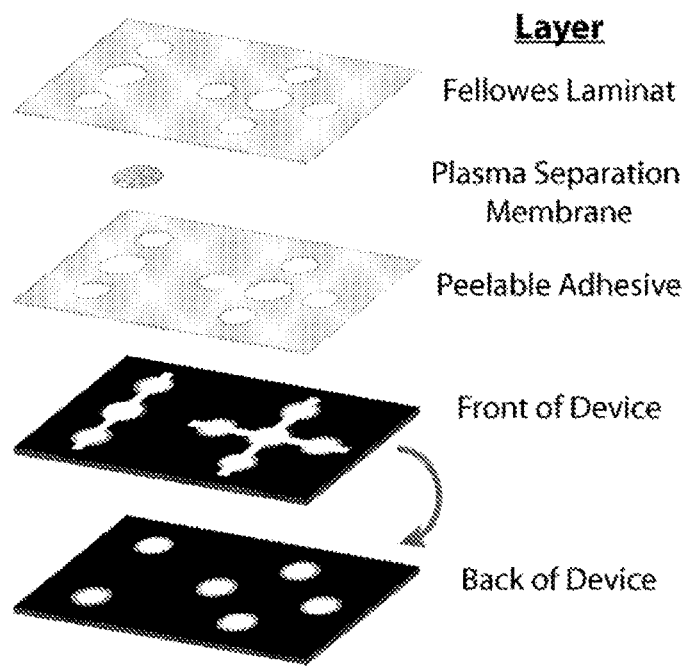
FIG. 12 shows a schematic depiction of a multilayer fluidic device, according to some embodiments.
Figure 13:
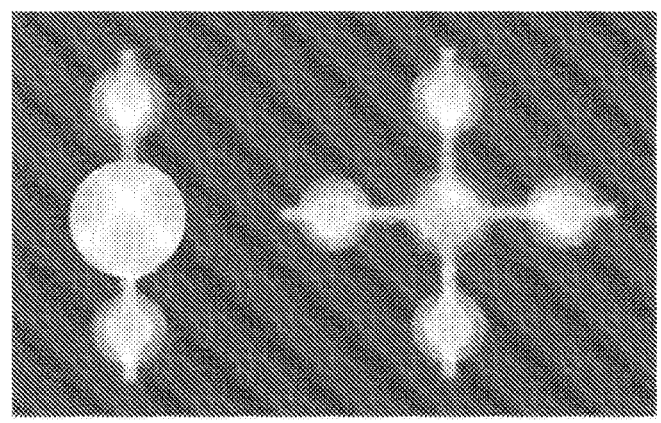
FIGS. 13-14 show photographs of a multilayer fluidic device prior to use thereof in which the sample regions and central region therein are highlighted, according to some embodiments.
Figure 14:
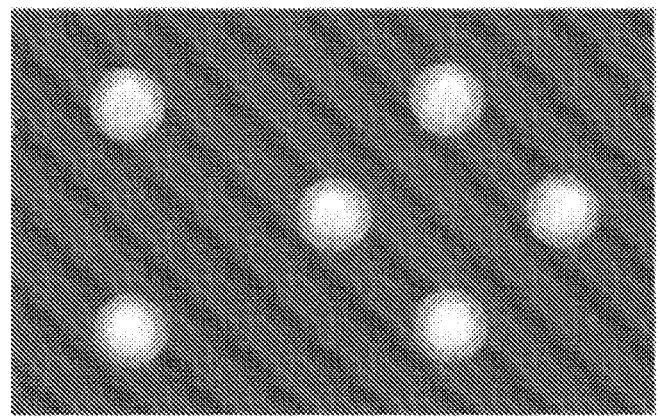
Figure 15:
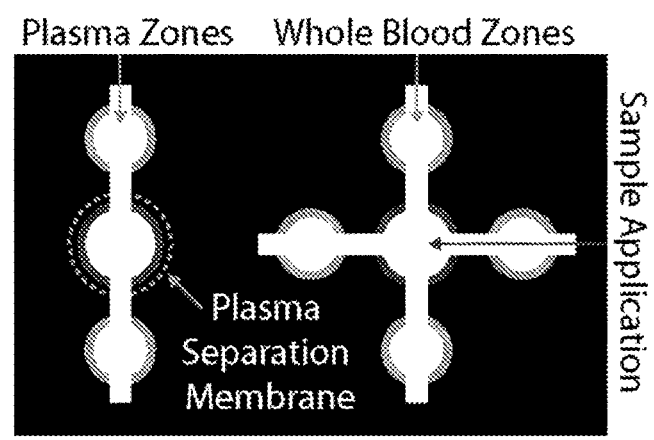
FIG. 15 shows a schematic depiction of the channels, sample regions, and central region of a multilayer fluidic device, according to some embodiments.
Figure 16:
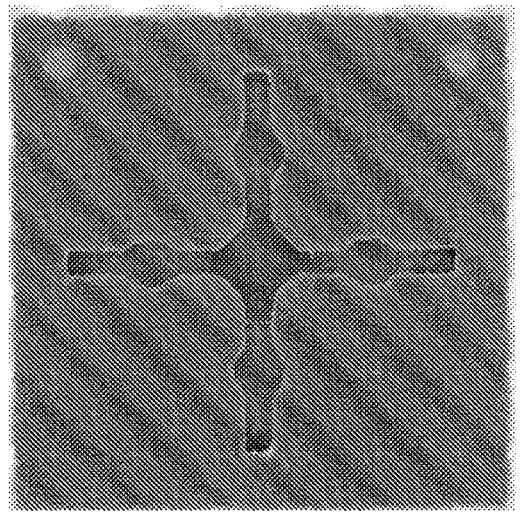
FIGS. 16-17 show photographs of a multilayer fluidic device after a blood sample has been flowed therethrough, according to some embodiments.
Figure 17:
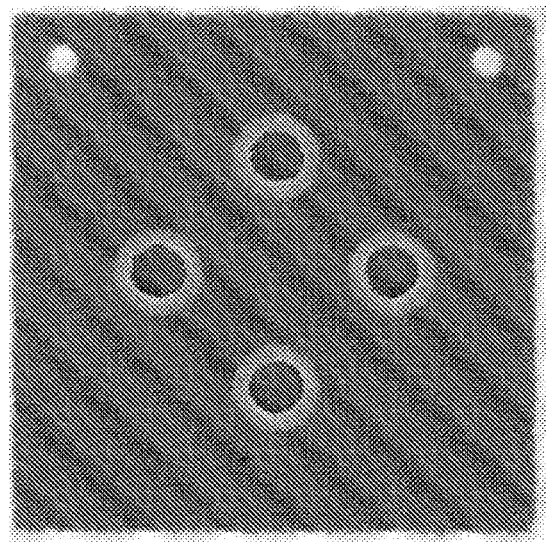

The multilayer fluidic device comprises a total of 4 layers. The layers include layers of porous, absorbent materials (referred to below as paper layers), layers that are configured to filter fluid (referred to below as filtration layers), adhesive layers, or cover layers. The narrative below describes the structure of each layer and how it is designed to interact with fluid samples introduced to the fluidic device. FIG. 12 shows an exploded view of the multilayer fluidic device. FIGS. 13-14 show photographs of the multilayer fluidic device prior to use thereof in which the sample regions and central region therein are highlighted. FIG. 15 shows a schematic depiction of the channels, sample regions, and central region of the multilayer fluidic device. FIGS. 16-17 show photographs of the multilayer fluidic device after a blood sample has been flowed therethrough.

Layer 1. A cover layer that is an adhesive film with eight cut-outs (e.g., regions in fluidic communication with an environment external to the fluidic device). The cut-outs expose central regions and sample regions in the paper layer below.

Layer 2. A filtration layer that separates blood cells from plasma. This material is affixed only to the left set of channels.

Layer 3. An adhesive layer with eight cut-outs. The adhesive adheres the layers between which it is positioned and the cut-outs allow for fluidic communication between the cut-outs in Layer 1 and the channels in Layer 4.

Layer 4. A paper layer comprising channels and sample regions. This layer is configured such that a fluid sample flowing into the layer is split into multiple samples that flow through the channels and are retained in the sample regions.

A fluidic device with the structure described above was designed in Adobe Illustrator and then fabricated by the procedure that follows. The channels and sample regions on the upper surface of layer 4 were formed by printing a hydrophobic barrier wax using a Xerox ColorQube 8580 printer onto a paper. After this step, the paper was pressed between two sheets of wax tracing paper for 45 seconds using a PromoHeat press (PRESS-CS-15) set at 280° F., during which the wax melted into the paper. The sample regions on the lower surface of the layer 4 were printed onto an adhesive film, the adhesive film was aligned with the lower surface of the paper with the aid of a light box, the adhesive film was taped onto the lower surface of the paper, and then the adhesive film and the paper were pressed between two sheets of wax tracing paper for 45 seconds using the PromoHeat press set at 280° C. An adhesive layer and a cover layer (a Fellowes laminating sheet) were cut with a Graphitec Cutting Plotter (CE6000-40) to form layers 3 and 1, respectively. Then, layers 1-4 were assembled together and laminated with a TruLam laminator.

Example 6

This Example describes the use of the multilayer fluidic device described in Example 5 to determine the potassium concentration in fluid samples.

Figure 18:
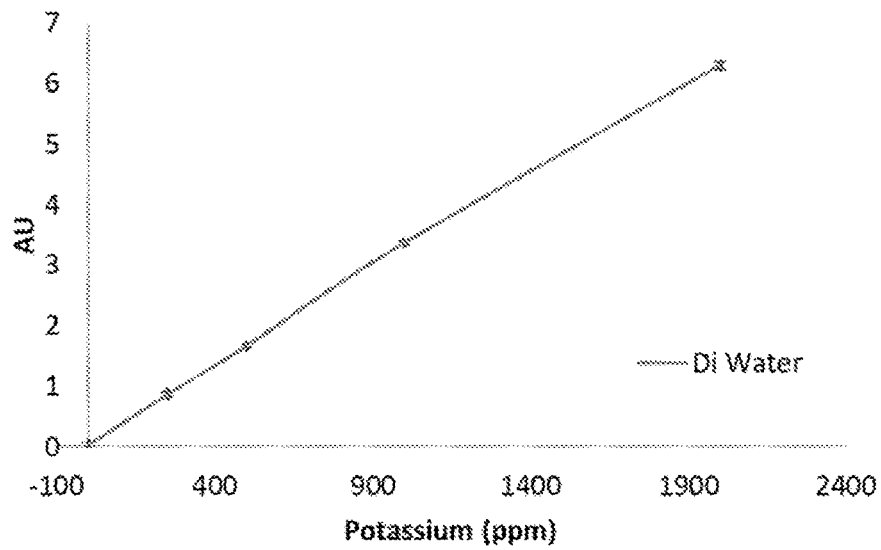
FIG. 18 shows measured absorbance as a function of potassium chloride concentration in the solutions applied to multilayer fluidic devices, according to some embodiments.

Five solutions of potassium chloride in deionized water at differing concentrations were applied to five of the multilayer fluidic devices described in Example 5. After application of the potassium chloride solutions thereto, the multilayer fluidic devices were dried at room temperature for 20 hours. Then, the sample regions therein were punched out with a single hole punch and each placed in separate 2 mL tubes containing 1.5 mL of deionized water. Next, these 2 mL tubes were rocked at 160 rpm for 10 minutes. After rocking, the water in the 2 mL tubes was diluted with further deionized water. The concentration of these diluted samples was measured by ICP-AES and compared to the absorbance of Ricca standards. FIG. 18 shows the measured absorbance as a function of potassium chloride concentration in the solutions applied to the multilayer fluidic devices.

Example 7

This Example describes the use of the multilayer fluidic device described in Example 5 to determine the concentration of bovine serum albumin in fluid samples.

Solutions of bovine serum albumin at differing concentrations in 1X phosphate-buffered saline were applied to fluidic devices having the structure described in Example 5. After application of the bovine serum albumin solutions thereto, the multilayer fluidic devices were dried at room temperature for 20 hours. Then, the sample regions therein were punched out with a single hole punch and each placed in separate 1.5 mL tubes containing 750 µL of deionized water and 750 µL of Pierce protein assay reagent. Next, these 1.5 mL tubes were rocked at 160 rpm for 5 minutes. After rocking, the absorbance at 660 nm of the fluid in the 1.5 mL tubes was measured with a UV-vis spectrophotometer.

Example 8

This Example describes the use of the multilayer fluidic device described in Example 5 to determine the concentration of hemoglobin in fluid samples.

Figure 19:
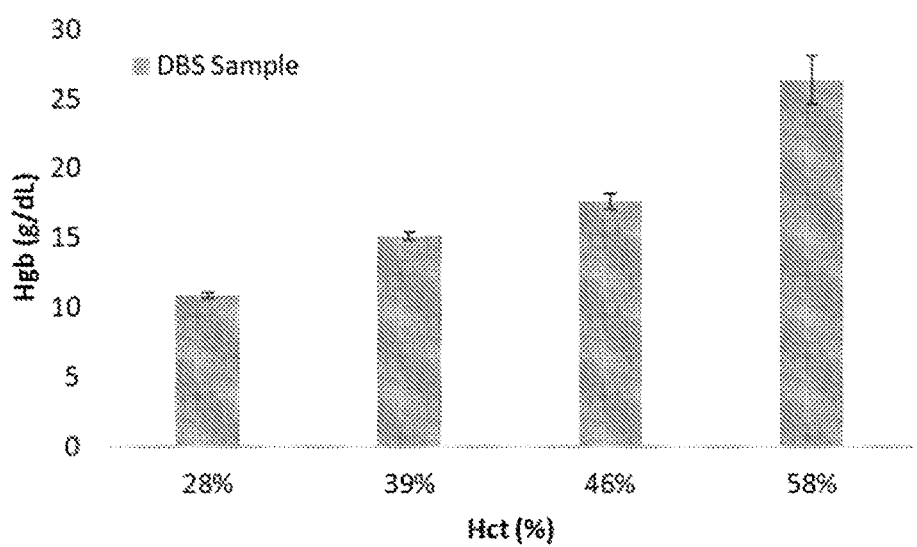
FIG. 19 shows hemoglobin concentration in hemoglobin standards determined based on the absorbance measurements as a function of hematocrit percentage in the hemoglobin standards, according to some embodiments.
Figure 20:
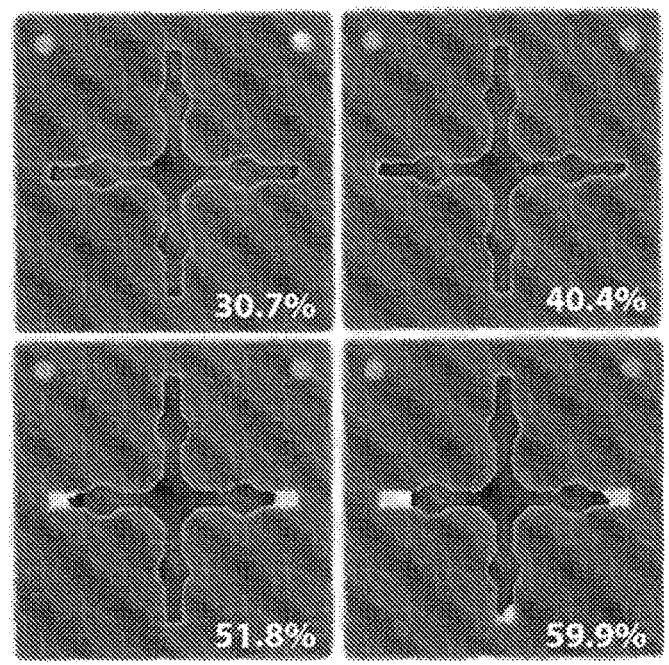
FIG. 20 shows photographs of multilayer fluidic devices after the application of hemoglobin standards thereto, according to some embodiments.

Samples of whole blood at different hematocrits having different hemoglobin concentrations were applied to fluidic devices having the structure described in Example 5. After application of the samples of whole blood thereto, the multilayer fluidic devices were dried at room temperature for 20 hours. Then, the sample regions therein were punched out with a single hole punch and each placed in separate 1.5 mL tubes containing 1 mL of Drabkin's reagent. Next, these 1.5 mL tubes were rocked at 160 rpm for 15 minutes. After rocking, the absorbance at 540 nm of the fluid in the 1.5 mL tubes was measured with a UV-vis spectrophotometer. FIG. 19 shows the hemoglobin concentration in the samples of whole blood determined based on the absorbance measurements as a function of hematocrit percentage therein. FIG. 20 shows photographs of the multilayer fluidic devices after the application of the samples of whole blood thereto. The number in the lower right of each image is the hematocrit percentage.

Example 9

Figure 21:
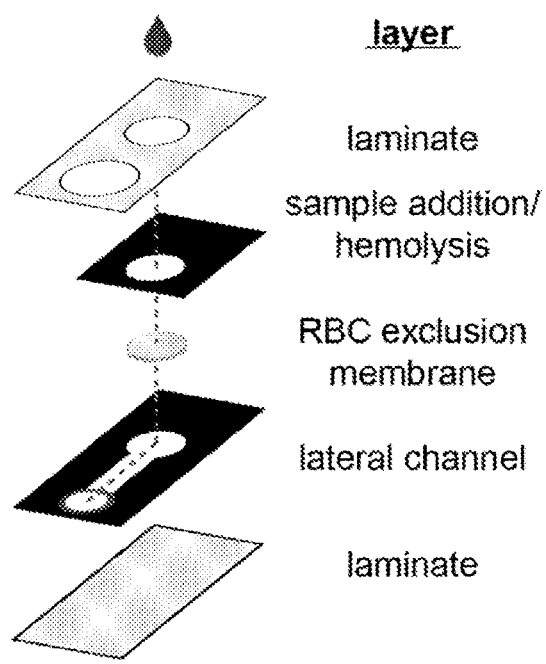
FIG. 21 shows an exploded view of a multilayer fluidic device, according to some embodiments.

This Example describes the design and fabrication of a multilayer fluidic device. The multilayer fluidic device comprises a total of 5 layers of porous, absorbent materials (referred to below as paper layers), layers that are configured to filter fluid (referred to below as filtration layers), or cover layers. The narrative below describes the structure of each layer and how it is designed to interact with fluid samples introduced to the fluidic device. FIG. 21 shows an exploded view of the multilayer fluidic device.

Layer 1. A cover layer that is an adhesive film with two cut-outs (e.g., regions in fluidic communication with an environment external to the fluidic device). The cut-outs expose a region at which a fluid sample is initially received and a sample region. The cover layer protects the stored reagents from environmental contaminants and user interference.

Layer 2. A paper layer comprising a region at which a sample is received.

Layer 3. A layer configured to filtration layer that separates blood cells from plasma. This material is affixed only beneath the region at which the sample is received in layer 2.

Layer 4. A paper layer comprising a channel.

Layer 5. A cover layer that is an adhesive film. The cover layer protects the stored reagents from environmental contaminants and user interference.

A fluidic device with the structure described above was designed in Adobe Illustrator and then fabricated by the procedure that follows. The channels and sample regions in the paper layers were formed by printing a hydrophobic barrier wax using a Xerox ColorQube 8580 printer onto Whatman chromatography papers (grade 4 with a 25 micron pore size). After printing, the papers were heated for 45 seconds using a Promo Heat press (PRESS-CS-15) set at 280° F., during which the wax melted through the full thickness of the paper. 6 µL of 50 wt %/vol saponin in 0.5 M ethylenediaminetetraacetic acid (pH 8.0) was then added to the paper to be employed as layer 2. After this step, this paper was dried at 65° C. for 5 minutes. Layer 3 was fabricated by using a 6 mm hole punch to cut out an appropriately-sized portion of a larger Pall GR Vivid plasma separation membrane. Next, sheets of Flexmount Select DF051521 double-sided adhesive were cut using a Graphtex Cutting Plotter (CE6000-40). The layers were assembled together with sheets of double-sided adhesive positioned therebetween, positioned between the cover layers (Fellowes laminating sheets), laminated with a TruLam laminator.

The paper and laminate sheets were purchased from Amazon. The saponin was purchased from EMD Millipore Corp. The plasma separation membrane was purchased from Pall. This membrane is a poly(sulfone) membrane including asymmetric pores that passively filters cells from whole blood to produce purified plasma. The asymmetric pore structure is believed to remove red blood cell membrane fragments and reduce clogging of the multilayer fluidic device following hemolysis. The ethylenediaminetetraacetic acid solution was purchased from Fisher Scientific. The double-sided adhesive was purchased from FLEXcon.

Example 10

This Example describes the use of the multilayer fluidic device described in Example 9 to determine the extent of hemolysis of blood therein.

The initial hematocrit of whole blood samples were measured upon arrival. This was performed by adding 3 µL of the whole blood to a 40 mm microhematocrit capillary tube and then sealing the tube at one end with Critoseal vinyl plastic putty. The sealed microhematocrit tubes were then centrifuged at 1,200 RPM for 3 minutes using a ZipCombo centrifuge from LW Scientific. After centrifugation thereof, the microhematocrit tubes were imaged using an 8-bit EPSON Perfection V600 PHOTO scanner having a resolution of 800 dpi. The images were analyzed to determine the hematocrit of each sample by measuring the ratio of the length that red blood cells occupied in the tube in the images to the total sample length in the images with ImageJ software. A total of n=2 replicates per measurement of hematocrit were performed for each sample.

The initial amount of hemoglobin in the whole blood samples was measured by adding 4 µL of whole blood to 1 mL Drabkin's reagent comprising 0.05% vol % Brij 35. This mixture was incubated at 25° C. for 15 minutes, after which its absorbance at 540 nm was measured using a Varioskan LUX microplate reader. Calibration curves for the amount of hemoglobin in the whole blood samples were prepared daily using a lyophilized hemoglobin standard rehydrated with deionized water (18 megohms) and then diluted to form solutions having a concentration ranging from 3-18 g/dL. The limit of detection (LOD) for the Drabkin's assay using isolated plasma (n=20) was also determined.

Figure 22:
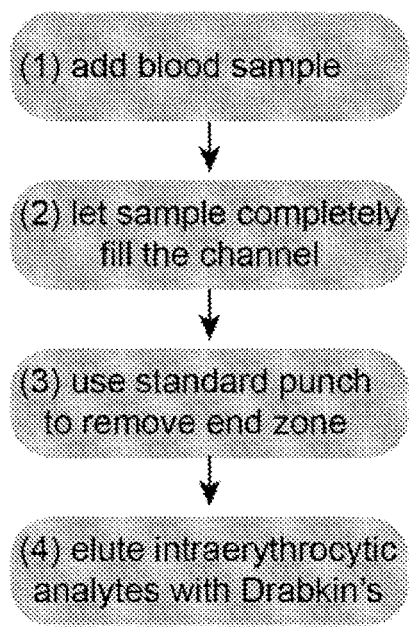
FIG. 22 shows a schematic depiction of a process of measuring hemolysis, according to some embodiments.

The extent of hemolysis in the multilayer fluidic device described in Example 9 was quantified by quantifying hemoglobin in the end zone of the lateral channel and comparing it to the total available hemoglobin in the sample. Blood samples were warmed to 37° C. and then 40 µL amounts thereof were added to multilayer fluidic devices having the design described in Example 9. Once the samples saturated the end zones of the lateral channels therein (in layer 4), a 5 mm diameter circle was removed from each end zone with a standard office hole punch. The intraerythrocytic contents were eluted from the punch in 1.0 mL of Drabkin's reagent for 30 minutes on a spin rotor. FIG. 22 shows a schematic depiction of this process, after which the absorbance of the resultant samples at 540 nm was measured using a Varioskan LUX microplate reader.

Figure 23:
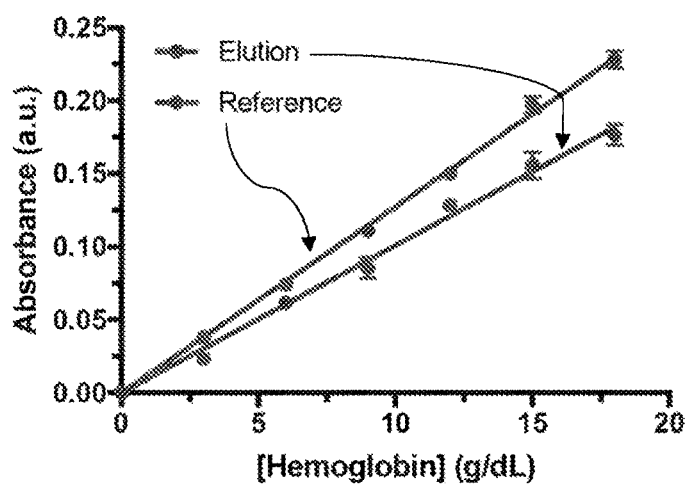
FIG. 23 shows calibration curves for the samples eluted from a multilayer fluidic device and from initial whole blood samples, according to some embodiments.

FIG. 23 shows calibration curves for the samples eluted from the multilayer fluidic device and from the initial whole blood samples. Each data point shown in FIG. 22 is the mean of five replicates, and the error bars shown in FIG. 22 represent the standard error of the mean. The best fit lines shown in FIG. 23 were fit to the data using linear regression (reference method: $R^2$=0.997, slope=0.0127; elution method: $R^2$=0.995, slope=0.0101).

The Drabkin's reagent and Brij 35 (30 wt %) were purchased from Ricca Chemical. The lyophilized hemoglobin was purchased from Pointe Scientific. The Critoseal was purchased from VWR. The 40 mm microhematocrit capillary tubes were purchased from LW Scientific. The whole blood samples were obtained from Research Blood Components.

Example 11

Figure 24:
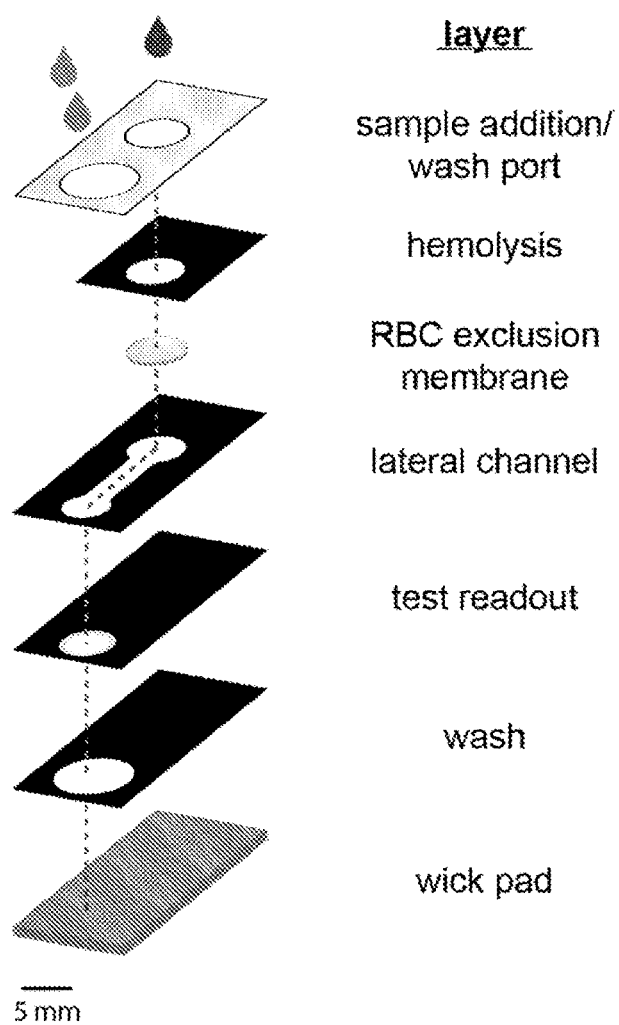
FIG. 24 shows an exploded view of a multilayer fluidic device, according to some embodiments.

This Example describes the design and fabrication of a multilayer fluidic device. The multilayer fluidic device comprises a total of 7 layers of porous, absorbent materials (referred to below as paper layers), layers that are configured to filter fluid (referred to below as filtration layers), or cover layers. The narrative below describes the structure of each layer and how it is designed to interact with fluid samples introduced to the fluidic device. FIG. 24 shows an exploded view of the multilayer fluidic device.

Layer 1. A cover layer that is an adhesive film with two cut-outs (e.g., regions in fluidic communication with an environment external to the fluidic device). The cut-outs expose a region at which a fluid sample is initially received and a wash port. The cover layer protects the stored reagents from environmental contaminants and user interference.

Layer 2. A paper layer comprising a region at which a sample is received.

Layer 3. A filtration layer that separates blood cells from plasma. This material is affixed only beneath the region at which the sample is received in layer 2.

Layer 4. A paper layer comprising a channel.

Layer 5. A paper layer comprising a sample region.

Layer 6. A paper layer that is used to collect excess sample, reagent, or wash solution.

Layer 7. A wick pad that is used to collect excess sample, reagent, or wash solution.

A fluidic device with the structure described above was designed in Adobe Illustrator and then fabricated by the procedure that follows. The channels, sample regions, and regions configured to collect excess sample, reagent, or wash solution in the paper layers were formed by printing a hydrophobic barrier wax using a Xerox ColorQube 8580 printer onto Whatman chromatography papers (grade 4 with a 25 micron pore size). After printing, the papers were heated for 45 seconds using a Promo Heat press (PRESS-CS-15) set at 280° F., during which the wax melted through the full thickness of the paper. 6 µL of 50 wt %/vol saponin in 0.5 M ethylenediaminetetraacetic acid was then added to the paper to be employed as layer 2. After this step, this paper was dried at 65° C. for 5 minutes and had a final concentration of saponin of 10.6 µg/cm$^2$. Layer 3 was fabricated by using a 6 mm hole punch to cut out an appropriately-sized portion of a larger Pall GR Vivid plasma separation membrane. An Ahlstrom 226 paper was used for the wick pad, as it is a thick material suitable for blotting. Next, sheets of a Flexmount Select DF051521 double-sided adhesive were cut using a Graphtex Cutting Plotter (CE6000-40). The layers were assembled together with sheets of double-sided adhesive positioned therebetween, positioned between the cover layers (Fellowes laminating sheets), laminated with a TruLam laminator.

The paper and laminate sheets were purchased from Amazon. The saponin was purchased from EMD Millipore Corp. The plasma separation membrane was purchased from Pall. This membrane is a polysulfone membrane including asymmetric pores that passively filters cells from whole blood to produce purified plasma. The asymmetric pore structure is believed to remove red blood cell membrane fragments and reduce clogging of the multilayer fluidic device following hemolysis. The ethylenediaminetetraacetic acid solution was purchased from Fisher Scientific. The double-sided adhesive was purchased from FLEXcon.

Example 12

This Example describes the use of the multilayer fluidic device described in Example 11 to determine the extent of hemolysis of blood therein.

The device is configured such that addition of whole blood thereto causes rehydration of the hemolytic reagent, saponin, for in situ hemolysis. Disruption of the red blood cell membrane by the hemolytic reagent causes the release of intraerythrocytic contents into the plasma from the red blood cells and results in an excess of membrane fragments. The plasma separation membrane of layer 3 is configured to retain these fragments to prevent clogging of the channels in the paper layers therebeneath. The plasma carrier fluid is then believed to facilitate the transportation of soluble, intraerythrocytic contents through the channel in layer 4 (an incubation channel) by capillary action. Layer 4 is configured such that the intraerythrocytic material mixes with the assay reagents stored therein before flowing to and being retained in the sample region (which also serves as a test readout zone). Layers 5 and 6 are configured to remove excess sample and wash buffer from the sample region in order to reduce background signal.

Hemolysate controls were prepared by mixing whole blood samples with a 50 wt %/vol saponin solution and then incubating the resultant mixture at 37° C. for 10 minutes. This mixture was then centrifuged for 5 minutes at an RCF of 800 g to sediment cellular membrane fragments, after which the supernatant was removed. The hemoglobin concentration in the supernatant was then quantified using methods described in Example 10 and had physiologically relevant ranges of hematocrits (25%-55%).

Figure 25:
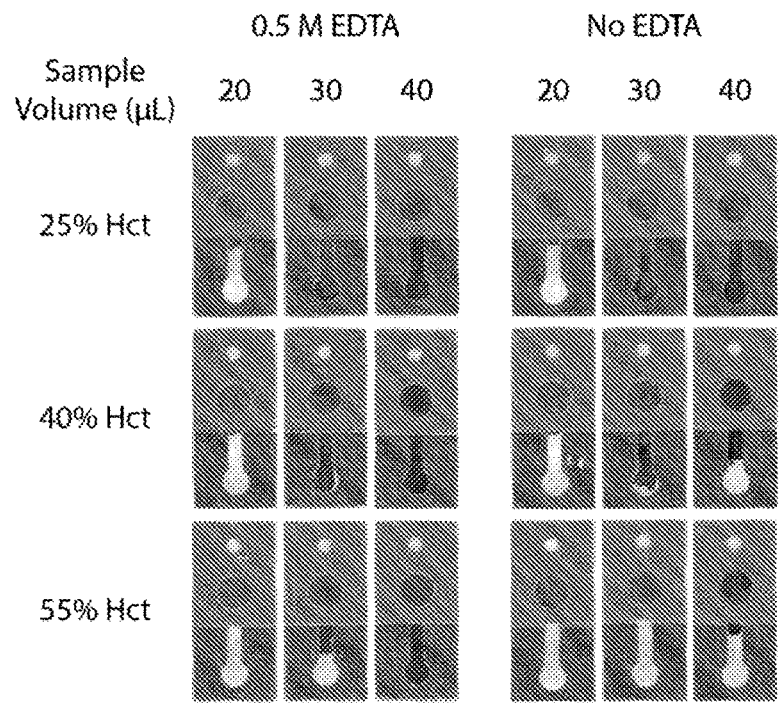
FIG. 25 shows photographs of multilayer fluidic devices, according to some embodiments.

These controls were added to the multilayer fluidic devices described herein. Initially, samples with high hematocrits (e.g., 55%) were not transported to the end of the channel in layer 4 for analysis due to coagulation thereof following the release of intraerythrocytic contents. Increasing the sample volume applied to the multilayer fluidic device from 20 µL to 40 µL increased sample flow, however, samples with hematocrits above 40% still did not reach the end zone. To decrease the effect of coagulation following hemolysis, an anti-coagulant was stored in the device. Treating the sample addition layer with 0.5 M ethylenediaminetetraacetic acid resulted in transportation of all hemolysate controls to the sample region at the end of the channel in layer 4 (regardless of hematocrit) when the sample volume of the hemolysate controls was 40 µL. Images of multilayer fluidic devices evidencing these results are shown in FIG. 25.

Figure 26:
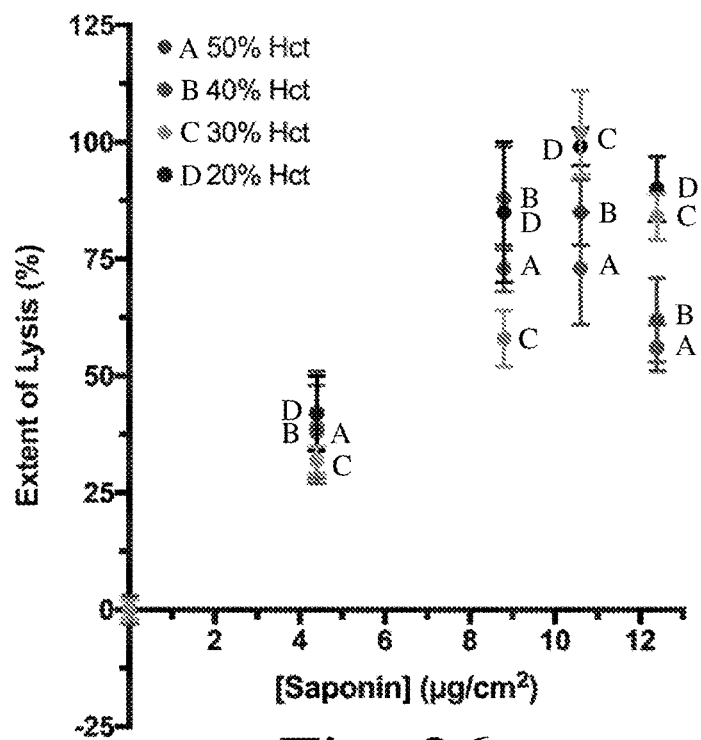
FIGS. 26-27 show the extent of lysis as a function of saponin concentration in multilayer fluidic devices, according to some embodiments.
Figures 27, 28:
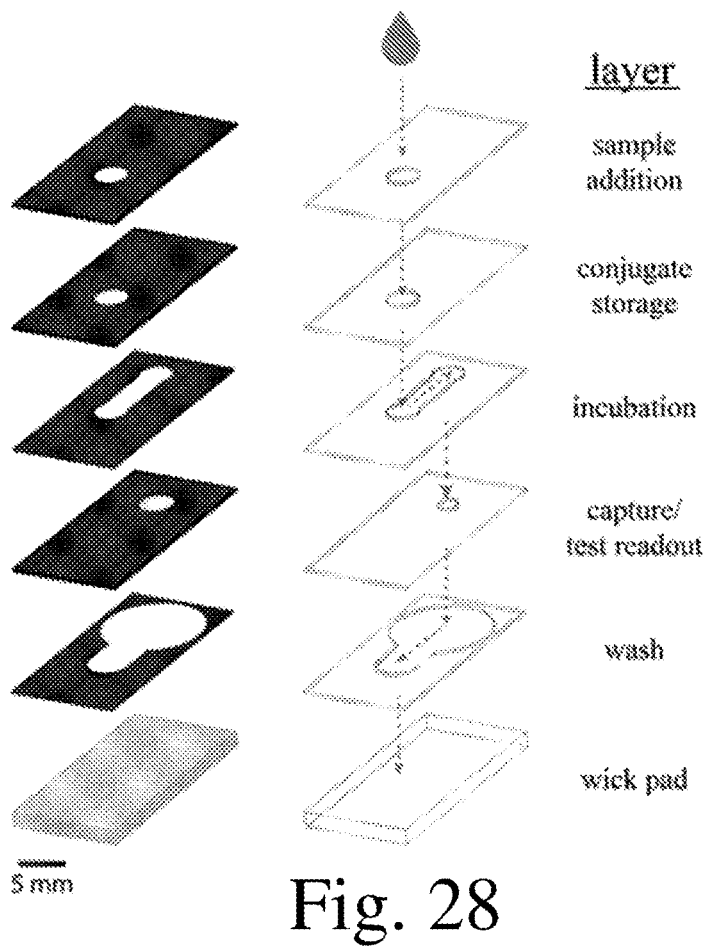
FIGS. 28-30 show three possible designs for multilayer fluidic devices, according to some embodiments.

Lysis conditions were achieved over a range of hematocrits (20-50%) by treating the fluidic device with 6 µL of 50 wt %/vol saponin (corresponding to 10.6 µg of saponin per cm$^2$). At 10.6 µg of saponin per cm$^2$, quantitative lysis was observed for whole blood samples with hematocrits below 40% while samples with hematocrits above 40% exhibited a lesser degree of hemolysis. It is believed that the decrease in hemolysis is due to the increased quantity of red blood cells present in samples of whole blood with elevated hematocrits. Increased concentrations of saponin resulted in a decrease in hemolysis for all samples. It is believed that rehydration of saponin decreases above this concentration, causing fewer red blood cell interactions with the saponin and yielding lesser hemolysis. FIGS. 26 and 27 show the extent of lysis as a function of saponin concentration per area with five replicates per data point. In FIG. 27, SEM refers to standard error of the mean.

Example 13

This Example shows further possible multilayer fluidic device designs and data therefrom.

Figure 29:
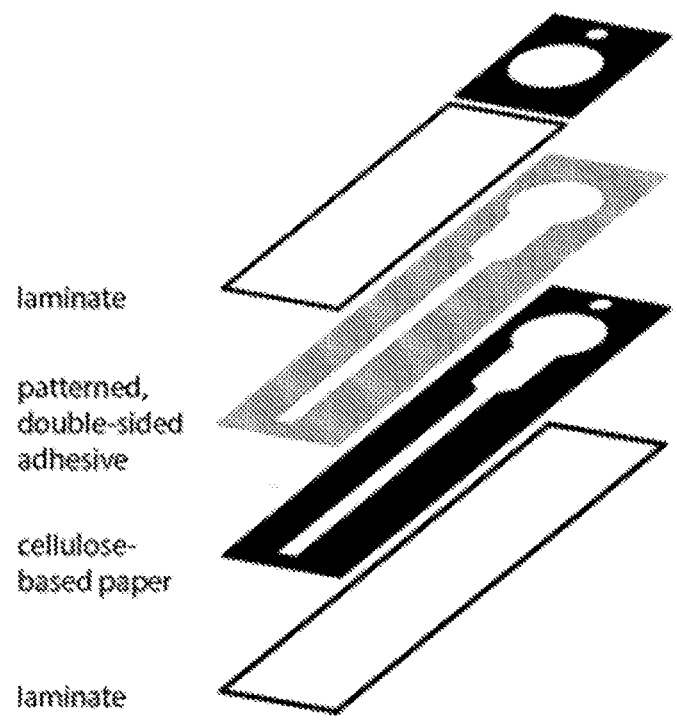
Figure 30:
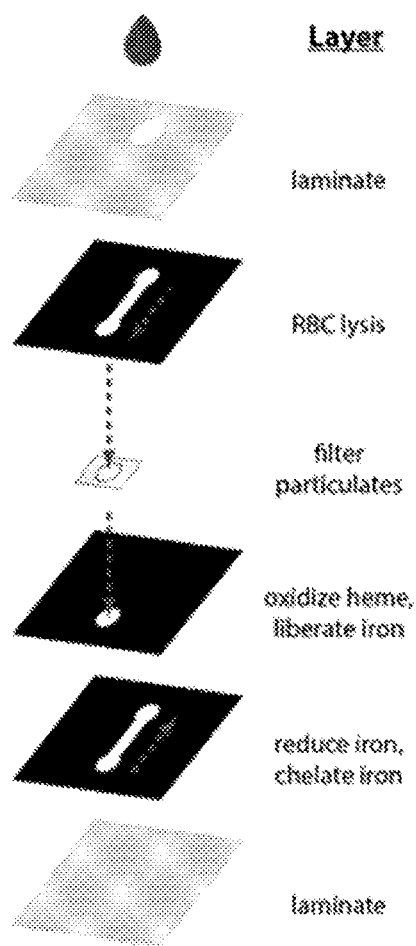

FIGS. 28-30 show three further possible designs for multilayer fluidic devices. Two or more of the multilayer fluidic devices shown in FIGS. 28-30 may be combined with each other, or the functionalities of two or more of these multilayer fluidic devices may be combined in a single device (e.g., as shown in FIG. 31).

Figure 31:
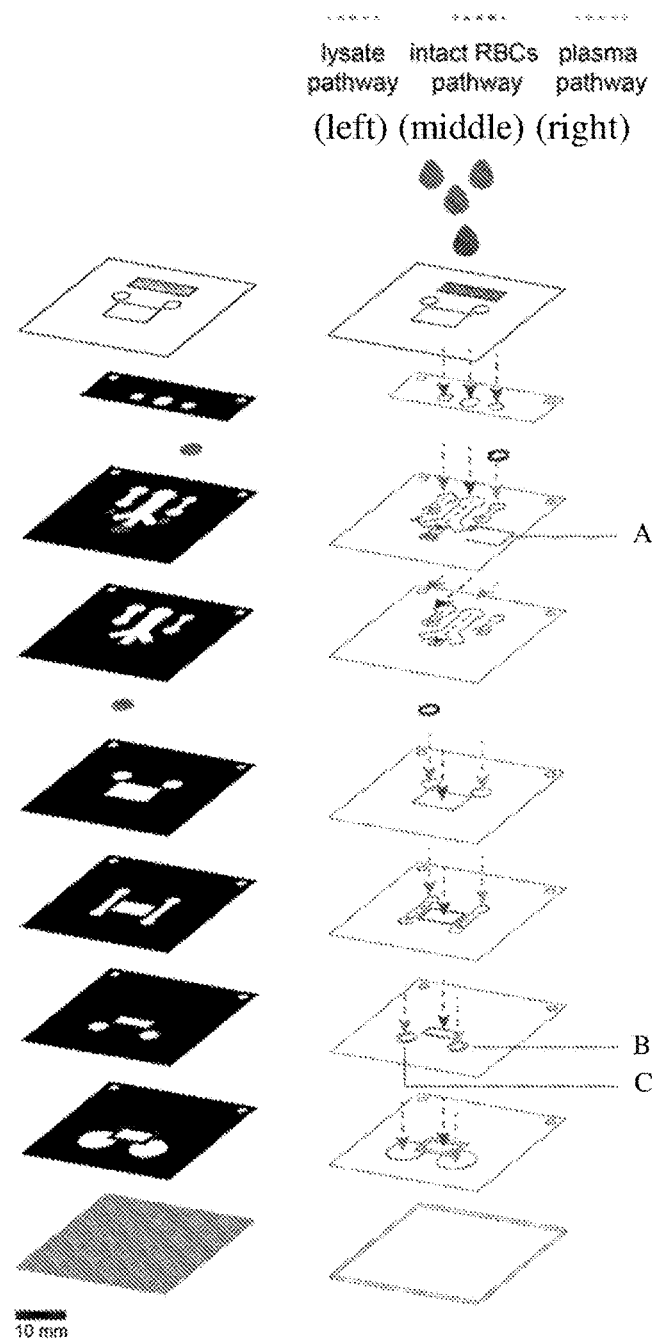
FIG. 31 shows an exploded view of a multilayer fluidic device, according to some embodiments.

Multilayer fluidic devices as shown in FIG. 31 were employed to determine the blood type and perform assays on blood samples. Three samples of 100 µL of 45% hematocrit whole blood were applied to three multilayer fluidic devices having the design shown in FIG. 31. After the multilayer fluidic devices were saturated with the whole blood, 150 µL of a wash buffer was applied to the wash inlet in fluidic communication with the sample region configured to perform blood typing and 50 µL of wash buffer was applied to a wash inlet in fluidic communication with a sample region configured to perform an immunoassay. The total process took 20 minutes.

Figure 32:
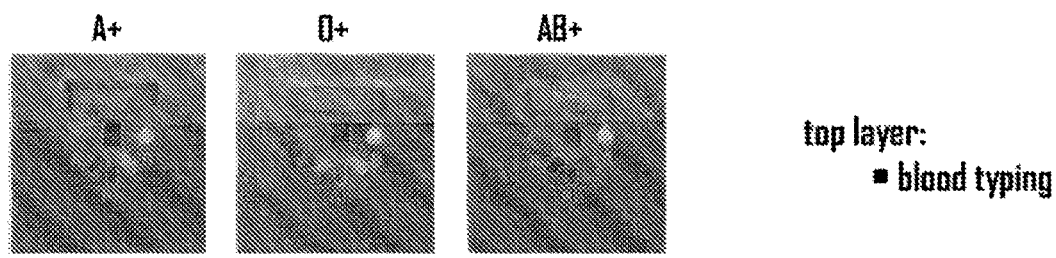
FIG. 32 shows the fourth layer of a multilayer fluidic device.
Figure 33:
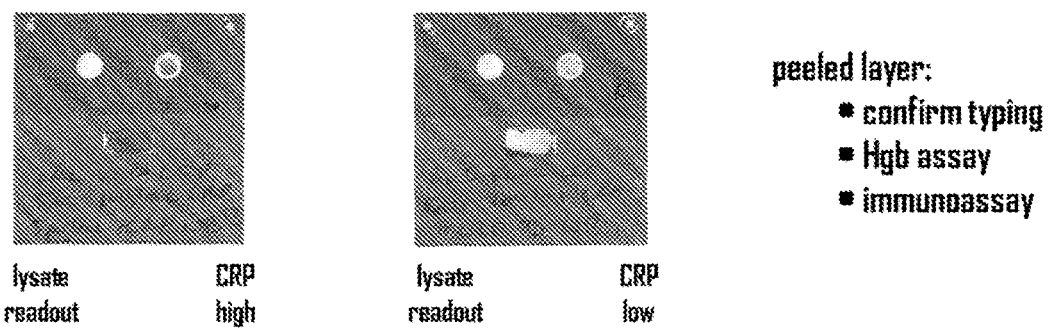
FIG. 33 shows the ninth layer of a multilayer fluidic device.

FIG. 32 shows the fourth layer of the multilayer fluidic devices after the above-described processes for A+, 0+, and AB+ blood samples. FIG. 33 shows the ninth layer of the multilayer fluidic devices after the above-described processes for high and low CRP samples, respectively.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A fluidic device, comprising:
   a first layer comprising a porous, absorbent material, wherein the first layer comprises:
   a central region in fluidic communication with an environment external to the fluidic device; and
   a first channel and a second channel in fluidic communication with the central region and extending radially outwards therefrom, wherein:

the first channel comprises a first sample region from which a first sample can be removed from the fluidic device, the second channel comprises a second sample region from which a second sample can be removed from the fluidic device, the first sample region extends laterally outwards from the rest of the first channel such that the first sample region is the widest part of the first channel, the second sample region extends laterally outwards from the rest of the second channel, and the first channel extends beyond the first sample region, such that:
  a first portion of the first channel is upstream from the first sample region;
  a second portion of the first channel is downstream from the first sample region; and
  the first sample region and the first sample are configured to be removed from the fluidic device together.

2. The fluidic device of claim 1, wherein the second channel terminates in the second sample region.

3. The fluidic device of claim 1, wherein the second channel extends beyond the second sample region.

4. The fluidic device of claim 1, wherein the first channel comprises a third sample region.

5. The fluidic device of claim 1, wherein the central region is separated from a portion of the fluidic device external to the central region by a barrier impermeable to a fluid.

6. The fluidic device of claim 1, wherein at least one of, or both of, the first and second channels are separated from a portion of the fluidic device external to the first and/or second channel(s) by a barrier impermeable to a fluid.

7. The fluidic device of claim 1, wherein at least one of, or both of, the first and second sample regions are separated from a portion of the fluidic device external to the first and/or second sample region(s) by a barrier impermeable to a fluid.

8. The fluidic device of claim 1 configured to receive a fluid, wherein the fluid is an aqueous fluid.

9. The fluidic device of claim 1, wherein the first layer comprising the porous, absorbent material further comprises a third channel in fluidic communication with the central region.

10. The fluidic device of claim 1, wherein the channels in fluidic communication with the central region are positioned radially symmetrically around the central region.

11. The fluidic device of claim 1, wherein a volume of the first channel is within 500% of a volume of the second channel.

12. The fluidic device of claim 1, wherein the fluidic device further comprises one or more additional layers.

13. The fluidic device of claim 1, wherein at least one of the first sample region and the second sample region can be removed from the fluidic device by use of a biopsy punch.

14. The fluidic device of claim 1, wherein the first channel and/or the second channel in fluidic communication with the central region is configured to transport plasma away from the central region.

15. The fluidic device of claim 1, further comprising a second, filtration layer configured to separate blood cells from plasma and positioned between the environment external to the fluidic device and the first layer, wherein the second, filtration layer is configured to retain at least 80% of cells from a blood sample on a first side.

16. The fluidic device of claim 1, further comprising a second, filtration layer configured to separate blood cells from plasma and positioned between the environment external to the fluidic device and the first layer, wherein the second, filtration layer is configured to lyse less than 50% of cells in a blood sample.

17. The fluidic device of claim 1, further comprising a second, filtration layer configured to separate blood cells from plasma and positioned between the environment external to the fluidic device and the first layer, wherein the second, filtration layer is reversibly attached to the first layer comprising the porous, absorbent material.

18. The fluidic device of claim 1, further comprising a second, filtration layer configured to separate blood cells from plasma and positioned between the environment external to the fluidic device and the first layer, wherein the second, filtration layer comprises asymmetric pores.

19. The fluidic device of claim 1, wherein the fluidic device comprises markings identifying the boundary of the first sample region.

20. The fluidic device of claim 1, wherein the first sample region is positioned such that blood having a hematocrit level of 25%-55% introduced into the fluidic device through the central region saturates the first sample region to substantially the same degree regardless of hematocrit level in this range.

* * * * *